United States Patent
Herrema et al.

(10) Patent No.: US 8,071,342 B2
(45) Date of Patent: *Dec. 6, 2011

(54) PROCESS FOR THE TREATMENT OF METHANE EMISSIONS

(75) Inventors: Markus Donald Herrema, Laguna Niguel, CA (US); Kenton Kimmel, Dana Point, CA (US)

(73) Assignee: Newlight Technologies, LLC, Long Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/064,603

(22) PCT Filed: Dec. 29, 2005

(86) PCT No.: PCT/US2005/047415
§ 371 (c)(1),
(2), (4) Date: Feb. 22, 2008

(87) PCT Pub. No.: WO2007/024255
PCT Pub. Date: Mar. 1, 2007

(65) Prior Publication Data
US 2008/0241886 A1    Oct. 2, 2008
US 2010/0255540 A2    Oct. 7, 2010

Related U.S. Application Data

(63) Continuation-in-part of application No. 11/208,808, filed on Aug. 22, 2005, now Pat. No. 7,745,197, which is a continuation-in-part of application No. 10/687,272, filed on Oct. 15, 2003, now Pat. No. 6,982,161.

(60) Provisional application No. 60/721,938, filed on Sep. 29, 2005, provisional application No. 60/603,857, filed on Aug. 24, 2004.

(51) Int. Cl.
*C12P 7/42* (2006.01)
*C12P 7/44* (2006.01)
*C12N 9/02* (2006.01)
*A62D 3/02* (2007.01)

(52) U.S. Cl. ...... 435/146; 435/142; 435/189; 435/262.5

(58) Field of Classification Search .................. 435/146, 435/142, 189, 262.5
See application file for complete search history.

(56) References Cited

U.S. PATENT DOCUMENTS
3,878,305 A    4/1975  Damico et al.
(Continued)

FOREIGN PATENT DOCUMENTS
WO    WO2007/024255    3/2007
(Continued)

OTHER PUBLICATIONS

Nichols et al., "Accumulation of poly-beta-hydroxybutyrate in a methane-enriched, halogenated hydrocarbon-degrading soil column: implications for microbial community structure and nutritional status," Hydrobiologia, 1989, vol. 176/177, pp. 369-377.*

(Continued)

*Primary Examiner* — Rosanne Kosson
(74) *Attorney, Agent, or Firm* — Knobbe, Martens, Olson & Bear LLP

(57) ABSTRACT

The invention relates generally to a system and method for the treatment of gaseous emissions comprising methane, and in one specific embodiment, to a system and method for the treatment of emissions through the use of methanotrophic microorganisms. Certain embodiments of the invention are particularly advantageous because they reduce environmentally-destructive methane emissions and produce harvestable end-products.

13 Claims, 6 Drawing Sheets

U.S. PATENT DOCUMENTS

| | | | |
|---|---|---|---|
| 4,101,533 | A | 7/1978 | Lafferty et al. |
| 4,375,515 | A | 3/1983 | Patel et al. |
| 4,524,569 | A | 6/1985 | Hanna |
| 4,562,245 | A | 12/1985 | Stageman |
| 4,968,611 | A | 11/1990 | Traussnig et al. |
| 5,344,766 | A | 9/1994 | Ramachandran et al. |
| H1430 | H | 4/1995 | Apel et al. |
| 5,434,062 | A | 7/1995 | Groleau et al. |
| 5,480,794 | A | 1/1996 | Peoples et al. |
| 5,487,834 | A | 1/1996 | Carman et al. |
| 5,642,630 | A | 7/1997 | Abdelmalek et al. |
| 5,727,903 | A | 3/1998 | Borray et al. |
| 5,747,584 | A | 5/1998 | Noda |
| 5,789,536 | A | 8/1998 | Liggat et al. |
| 5,842,357 | A | 12/1998 | Siwajek et al. |
| 5,849,894 | A | 12/1998 | Clemente et al. |
| 5,871,980 | A | 2/1999 | Naylor et al. |
| 5,894,062 | A | 4/1999 | Liddel |
| 5,942,597 | A | 8/1999 | Noda et al. |
| 6,043,063 | A | 3/2000 | Kurdikar et al. |
| 6,051,411 | A | 4/2000 | Turtakovsky et al. |
| 6,205,704 | B1 | 3/2001 | Schmitz et al. |
| 6,395,520 | B1 | 5/2002 | Babel et al. |
| 6,446,385 | B1 | 9/2002 | Crutcher |
| 6,599,423 | B2 | 7/2003 | Boles et al. |
| 6,666,027 | B1 | 12/2003 | Cardenas, Jr. |
| 6,709,849 | B2 | 3/2004 | Cheung |
| 6,749,368 | B2 | 6/2004 | Ankeny et al. |
| 6,770,464 | B2 | 8/2004 | Steinbuchel et al. |
| 6,982,161 | B1 | 1/2006 | Herrema |
| 7,098,298 | B2 | 8/2006 | Kinoshita et al. |
| 7,141,400 | B2 | 11/2006 | Yu |
| 7,455,999 | B2 | 11/2008 | Madison et al. |
| 7,504,556 | B2 | 3/2009 | Madison et al. |
| 7,524,659 | B2 | 4/2009 | Nomoto et al. |
| 7,527,963 | B2 | 5/2009 | Nomoto et al. |
| 7,579,176 | B2 | 8/2009 | Herrema et al. |
| 7,641,706 | B1 | 1/2010 | McMurry et al. |
| 7,745,197 | B1 | 6/2010 | Herrema et al. |
| 7,887,893 | B2 | 2/2011 | Billington et al. |
| 2007/0141660 | A1 | 6/2007 | Chotani et al. |
| 2007/0202581 | A1 | 8/2007 | Herrema et al. |
| 2008/0160569 | A1 | 7/2008 | Ho et al. |
| 2009/0176900 | A1 | 7/2009 | Hirose et al. |
| 2009/0203093 | A1 | 8/2009 | Steinbuchel et al. |
| 2009/0226962 | A1 | 9/2009 | Huisman et al. |
| 2009/0317879 | A1 | 12/2009 | Criddle et al. |
| 2010/0093043 | A1 | 4/2010 | Huisman et al. |
| 2010/0190221 | A1 | 7/2010 | Herrema et al. |

FOREIGN PATENT DOCUMENTS

| | | |
|---|---|---|
| WO | WO2008/103134 | 8/2008 |

OTHER PUBLICATIONS

Co-Pending U.S. Appl. No. 11/208,808, filed Aug. 22, 2005. Title: Process for the Utilization of Ruminant Animal Methane Emissions.

Bioremediation—field Experience: Field Experience, Paul E. Flathman, Douglas E. Jerger and Jurgen H. Exner, CRC Press, Boca Raton, Florida, 1994, pp. 275-276.

Brigmon, Methanotrophic Bacteria: Use in Bioremediation, Westinghouse Savannah River Company, on-line publication No. WSRC-MS-2001-00058, http://sti.srs.gov/fulltext/ms2001058/ms2001058.html,2001.

Climate Change 2001: Working Group I: The Scientific Basis, Intergovernmental Panel on Climate Change, http://www.grida.no/climate/ipcc_tar/wg1/017.htm, 2001.

Gay, S.W., "Natural ventilation for freestall dairy barns," Pub. No. 442-763, Virginia Cooperative Extension, Virginia Polytechnic institute and State university, http://www.ext.vt.edu/pubs/bse/442-763/442-763.pdf, 2002.

Gooch, Curt A., Natural or Tunnel Ventilation of Freestall Structures: What is Right for Your Dairy Facility? www.milkproduct.com, Published Nov. 4, 2005.

Murrell et al., "Regulation of expression of methane monooxygenases by copper ions," Trends in Microbiology 8(5):221-225, 2000.

Tyson, John T. et al., Tunnel Ventilation for Tie Stall Dairy Barns, Penn State, College of Agricultural Sciences, Agricultural and Biological Engineering, 2nd Edition Jan. 1, 2004.

3. How can livestock methane emissions be reduced? Ruminant Livestock (Mar. 2007). http://www.epa.gov/methane/rlep/faq.html.

Bartle, "Exploiting a Gascating Bacteria," University of Bergen Magazin, 2002, at http://www.uib.no/elin/elpub/uibmag/en02/bacteria.html.

Cow Power, htt://www.riverdeep.net/current/2002/03/032502t_cowpower.jhtml, Mar. 2002.

D'Aquino, "Methane to Protein," at http://www.aptagen.com/corporate/AptagenDocunnents/Articles/che.html, 2000.

Gasser, "Agricultural productivity and the nitrogen cycle," Phil Trans R. Soc Lond. B296;303-314, 1982.

Johnson et al., "Methane emissions from cattle," J. Anim. Sci. 73:2483-2492, 1995.

Polakovic, "Getting the Cows to Cool It," Los Angeles Times, Jun. 7, 2003, pp. A1-A17, Los Angeles, CA U.S.A.

Wendlandt et al., "Producing poly-3-hydroxybutyrate with a high molecular mass from methane," J. Biotechnol. 2001, vol. 86, pp. 127-133, see pp. 127-128.

International Preliminary Report on Patentability of PCT Application No. PCT/US05/47415, 2008.

International Search Report and Written Opinion of PCT Application No. PCT/US05/47415, 2006.

Matter 2.0 (Jul. 1999). 5.1.1 Enteric fermentation (p. 22). ftp://ftp.ecn.nl/pub/www/library/report/1999/c99048.pdf.

Meeting Minutes of Methane to Markets, Agriculture Task Force Meeting dated Jun. 22, 2005. http://www.methanetomarkets.org/resources/ag/docs/ag-meeting.pdf.

Methane Emissions from Livestock Enteric Fermentation (p. 150). Reducing Emissions of Non-CO2 Greenhouse Gases (Sep. 2006). http://www.climatetechnology.gov/stratplan/final/CCTP-StratPlan-Ch07-Sep-2006.pdf.

Nichols, Peter D., and White, D.C., "Accumulation of poly-B-hydroxybutyrate in a methane-enriched, halogenated hydrocarbon-degrading soil column: implications for microbial community structure and nutritional status". Hydrobiologia 1989, 176/177:369-377.

Technologies for Reducing Non-Energy-Related Emissions (Mar. 2006). Enteric Fermentation (p. 8). http://www.cfses.com/documents/climate/10_%20Jolley_Technologies_for_Reducing_Non-energy_Related_Emissions.pdf.

The abatement challenge for Australian Agriculture (2007). Enteric methane (p. 2). http://www.dpc.vic.gov.au/CA256D800027B102/Lookup/Forum1EckardPaper/$file/Eckard%2017%20August%20202007%20-%20The%20abatement%20challenge%20for%20agriculture.pdf.

McDonald et al., "The Soluble Methane Monooxygenase Gene Cluster of the Trichloroethylene-Degrading Methanotroph Methylocystis sp. Strain M," Applied and Environmental Microbiology, 1997, vol. 63, pp. 1898-1904.

Wendlandt et al., "Possibilities for controlling a PHB accumulation process using various analytical methods," J. of Biotechn. 2005, vol. 117, pp. 119-129.

Co-pending U.S. Appl. No. 12/546,138, filed Aug. 24, 2009. Title: Method for Producing Polyhydroxyalkanoic Acid. Inventors: Markus Herrema et al.

Frans-Jaco, et al., "Spatial Distribution and Inhibition by Ammonium of Methane Oxidation in Intertidal Freshwater Marshes" Applied and Environmental Microbiology, (1997) vol. 63(12): 4734-4740.

Jensen, S. et al., "Methanol Improves Methane Uptake in Starved Methanotrophic Microorganisms" Applied and Environmental Microbiology, (1998) vol. 64(3): 1143-1146.

Norferm's future under discussion; Scandinavian Oil-Gas Magazine; http://www.scandoil.com/moxie-bm2/news/company_news/norferms-future-under-dis.shtml, Published Oct. 27, 2005.

International Search Report and Written Opinion of PCT Application No. PCT/US07/04484.

PCT International Search Report for PCT/US2010/047052 mailed Dec. 27, 2010).

Dias, et al., "Recent Advances in Polyhydroxyalkanoate Production by Mixed Aerobic Cultures: From the Substrate to the Final Product." Macromol. Biosci. (2006) 6, 885-906.

Singh et al., "*Bacillus subtilis* as potential producer for polyhydroxyalkanoates." BioMed Central. Microbial Cell Factories. Jul. 20, 2009, vol. 8, No. 38, pp. 1-11.

Verlinden, et al., "Bacterial synthesis of biodegradable polyhydroxalkanoates," Journal of Applied Microbiology, 102 (2007), p. 1437-1449.

Deublein, et al. "Biogas from Waste and Renewable Resources", pp. V-XIII, Part III, Chapter 2.1.1, p. 94, Wiley-VCH Verlag GmbH & Co. KgaA, Weinheim, 2008.

Frigon, et al. "rRNA and Poly—Hydroxybutyrate Dynamics in Bioreactors Subjected to Feast and Famine Cycles" Applied and Environmental Microbiology, Apr. 2006, p. 2322-2330.

Lee, et al. "High-density algal photobioreactors using light-emitting diodes" Biotechnology and Bioengineering, vol. 44, Issue 10, pp. 1161-1167, 1994.

Müller, et al. "Adaptive responses of Ralstonia eutropha to feast and famine conditions analysed by flow cytometry" J Biotechnol. Oct. 8, 1999;75(2-3):81-97.

Reis, et al. "Production of polyhydroxyalkanoates by mixed microbial cultures" Bioprocess and Biosystems Engineering, vol. 25, No. 6, 377-385, DOI: 10.1007/s00449-003-0322-4, 2003.

Co-pending U.S. Appl. No. 12/825,277, filed Jun. 28, 2010. Title: Process for the Utilization of Ruminant Animal Methane Emissions. Inventors: Markus Herrema et al.

\* cited by examiner

PROCESS FOR THE TREATMENT OF METHANE EMISSIONS

RELATED APPLICATIONS

This application is the U.S. National Phase application under 35 U.S.C. §371 of International Application PCT/US2005/047415 filed Dec. 29, 2005, (published as WO 2007/024255), which claims the benefit of Provisional Application No. 60/721,938, filed Sep. 29, 2005, and is a continuation-in-part of co-pending patent application Ser. No. 11/208,808, filed Aug. 22, 2005, which claims the benefit of Provisional Application No. 60/603,857, filed Aug. 24, 2004; wherein patent application Ser. No. 11/208,808 is a continuation-in-part of co-pending patent application Ser. No. 10/687,272, filed Oct. 15, 2003, now issued as U.S. Pat. No. 6,982,1617; and wherein the disclosures of all of these applications are incorporated by reference herein.

BACKGROUND OF THE INVENTION

1. Field of Invention

This invention relates generally to a system and method for the treatment of methane emissions, and in one specific embodiment, to a system and method for the treatment of methane emissions through the use of methanotrophic microorganisms.

2. Description of the Related Art

Methane emissions, or methane off-gases, are generated by a variety of natural and human-influenced processes, including anaerobic decomposition in solid waste landfills, enteric fermentation in ruminant animals, organic solids decomposition in digesters and wastewater treatment operations, and methane leakage in fossil fuel recovery, transport, and processing systems. As a particularly potent greenhouse gas, methane emissions are responsible for about twenty percent of planetary warming, and thus represent a significant environmental concern. Accordingly, there have been numerous efforts in the past to remediate, control, and/or otherwise treat methane emissions.

In addition to processing methane that is emitted from landfills, coal mines, wastewater treatment plants, manure digesters, agricultural digesters, compost heaps, enclosed agricultural feedlots, leaking or otherwise emitting petroleum systems, several embodiments of the present invention are directed to capturing and processing methane emitted by ruminant animals. Methane emissions from ruminant animals account for about twenty percent of total global methane emissions, and atmospheric methane accounts for about twenty percent of planetary warming. In addition to the environmentally destructive effects of ruminant animal methane emissions, such emissions represent wasted energy, as a significant percentage of the food ruminant animals eat is lost as methane. Accordingly, there have been significant efforts in the past to reduce ruminant animal methane emissions.

Ruminant animal methane emissions or, more specifically, enteric fermentation methane emissions, originate in the four-stomach digestive tract common to all ruminant animals, which includes the rumen, a large forestomach connected to the four-stomach digestive tract. The rumen contains a host of digestive enzymes, fungi, bacterium, and protozoa, and the bulk of digestion, as well as methane production via enteric fermentation, takes place here. Not surprisingly, all prior efforts to reduce enteric fermentation methane emissions from ruminant animals, which include dairy cows, beef cattle, sheep, goats, water buffalo, and camels, have focused on modifications associated with the rumen or digestive tract.

Several methods are known for the treatment of natural and human-influenced methane emissions Used in conjunction with well-known methane emissions collection methods, such as landfill gas extraction wells/blowers and coal mine methane ventilation systems, the treatment of air containing captured methane emissions includes the use of turbines, microturbines, engines, reverse-flow reactors, fuel cells, and boilers to convert methane emissions into heat and/or electricity. Other well-known methods for the treatment of methane emissions include the conversion of methane emissions into pipeline-quality, liquefied, or compressed natural gas.

The treatment and utilization of methane off-gases for the production of fuel, heat, and/or electricity is described by a number of patents, including U.S. Pat. Nos. 5,642,630, 5,727,903, 5,842,357, 6,205,704, 6,446,385, and 6,666,027, herein incorporated by reference. U.S. Pat. No. 5,642,630 describes the use of landfill gas to produce high quality liquefied natural gas, liquefied carbon dioxide, and compressed natural gas products. U.S. Pat. No. 5,727,903 describes the use of landfill gas to create vehicle grade fuel. U.S. Pat. No. 5,842,357 describes the use of landfill gas to create high grade fuel and food-grade carbon dioxide. U.S. Pat. Nos. 6,205,704 and 6,446,385 describe the use of landfill gas to provide heat, electricity, and/or carbon dioxide to enhance greenhouse operations. U.S. Pat. No. 6,666,027 describes the use of off-gas from landfills and digesters to power turbines for electricity generation.

Although each of these methods is effective at treating methane emissions under a specific range of conditions, none are known to be economically and/or technologically feasible under a range of sub-optimal methane-in-air conditions, including conditions where the flow rate, concentration, or purity of methane gas emissions is variable, unpredictable, low, and/or otherwise unfavorable.

Methane-utilizing, or methanotrophic, microorganisms are well-known in the microbiology art for their capacity to grow and reproduce using methane as a source of carbon and/or energy, particularly in a wide range of diverse methane availability conditions. Accordingly, methanotrophic microorganisms have been proposed in the past as a potential tool for the remediation of methane emissions, particularly in conditions where other treatment methods are technologically and/or economically unfeasible.

Two methods have been proposed for the utilization of methanotrophic microorganisms to treat methane emissions. In one proposed process, methanotrophic microorganisms are naturally present or purposefully situated in high-methane emissions environments, such as landfill covers or coal mines, are provided with growth-stimulating nutrients, such as oxygen, water, or mineral salts, to encourage increased microbial methane emission uptake rates. This method may be carried out using nutrient injection methods such as air or water sparging to induce increased methanotrophic growth and oxidation rates in high emissions environments. U.S. Pat. No. 6,749,368, for example, describes methanotrophic microorganisms that are placed in an aerated soil cover above a municipal landfill in order to oxidize and reduce methane emissions.

In a second proposed process, air containing methane emissions is diverted into an environment containing methanotrophic microorganisms in order to cause the microbial breakdown of methane emissions. This method may be carried out by diverting air containing methane emissions into a biofiltration column containing methanotrophic microorganisms, water, and a microorganism growth medium, whereby electricity, water, nitrogen, trace minerals, and other materials are continuously added to and consumed by the system in order to effect the microbial breakdown of methane emissions.

Both of these prior methanotrophic treatment techniques cannot effectively or efficiently reduce methane emissions. Indeed, the application of these processes has been precluded in practice because while both generate continuous and costly requirements for supply-limited materials, such as electricity and minerals, neither generates direct economic benefits to recover the capital costs of treatment, and the use of methanotrophic microorganisms for the treatment of methane emissions is simply too costly to operate and sustain over time. Prior to the applicants' discovery, no methods were known to enable the practical sustainability of the biological treatment of methane emissions, and, accordingly, the utilization of methanotrophic microorganisms for the treatment of methane emissions has been precluded in practice.

Accordingly, there exists a significant need to develop a system that enables methanotrophic methane emissions treatment to be technologically, financially, and logistically sustainable and, thus, viable in practice

SUMMARY OF THE INVENTION

Preferred embodiments of the present invention address the need for a system that enables methane emissions treatment to be technologically, financially, and logistically sustainable and viable. Prior to applicants' invention, gaseous emissions comprising methane have never been used in conjunction with methanotrophic microorganisms to effectively reduce the amount of environmentally destructive methane pollution and to create a harvestable product from that methane.

In one preferred embodiment, the gaseous emissions (which comprise some amount of methane) from landfills, coal mines, agricultural sites, or petroleum sites are captured and conveyed to a bioreactor containing methanotrophic microorganisms. The gaseous emissions do not need to undergo substantial purification. The microorganisms use the methane as a source of carbon or energy, and, in some embodiments produce useful end-products such as polymers. The polymers can then be used to synthesize various types of biodegradable materials. For example, the polymers can be used to produce plastics because, in some cases, the physical properties of the polymers produced by the methanotrophic microorganisms are very similar to those of polypropylene. However, the polymers produced by the methanotrophic microorganisms are biodegradable, and therefore environmentally friendly. Thus, some preferred embodiments of the invention offer a tremendous benefit to the environment in at least two ways: first, methane emissions are substantially reduced on the front end, and second, a biodegradable polymer is produced in useful quantities as the end-product.

The term "gaseous emission" as used herein shall mean off-gases and/or gases emitted by natural and/or human-influenced processes, including anaerobic decomposition in solid waste landfills, enteric fermentation in ruminant animals, organic decomposition in digesters and wastewater treatment operations, agricultural sites, and in fossil fuel recovery, transport, and processing systems.

Although the prior art recognized that methanotrophic organisms could use methane to produce polymers, the prior art did not teach or suggest an effective method by which destructive gaseous emissions that comprise methane could be used to produce polymers. Thus, prior to applicants' invention, the production of useful quantifies of polymers by methanotrophic organisms was not feasible, because the process, which (among other drawbacks) required a pure and/or concentrated source of methane, could only be done on a small scale. Moreover, because a pure and/or concentrated source of methane was required, the costs of operating the system was extremely high. Preferred embodiments of the present invention, however, do not require an artificial laboratory grade methane as the primary source of carbon or energy for the methanotrophic organisms. Instead, environmentally destructive gases that are already present in the environment can be used as the source of methane.

Moreover, preferred embodiments of the present invention are particularly advantageous because they can use gaseous emissions comprising low concentrations of methane, rather than pure methane. Although certain turbine systems can convert gaseous emissions into energy, the concentration of methane must be high. Although certain fuel cells can use methane in low concentrations, gaseous emissions cannot be used (the methane must be substantially pure). In one preferred embodiment of the current invention, gaseous emissions comprising methane in a concentration of less than about 40%, less than about 30%, less than about 20%, less than about 10%, less than about 5%, and less than about 1% can be used. Thus, several embodiments of the present invention are particularly useful for older landfills, which may produce methane in concentrations of about 0.1% to less than about 20% of total gaseous emissions as they age. Likewise, several embodiments of the present invention are particularly useful for coal mines, which may produce methane in concentrations of less than about 5% of total gaseous emissions, and in some cases about 1% methane. Thus, without the benefit of certain preferred embodiments of applicants' invention, these polluting systems—which alone produce methane as a small part of their total gaseous emissions—cumulatively contribute significantly to the total amount of methane in the environment and thus ultimately to the greenhouse effect.

In one embodiment of the invention, the system comprises means to enable the practical application of methanotrophic microorganisms to methane emissions treatment, particularly in a manner that does not rely on a reduction in the operating costs of treatment. In other words, in one embodiment, methanotrophic microorganisms can be used to reduce methane pollutants in the environment without relying on altering the methanotrophic microorganisms (e.g., by genetic engineering, etc.). In one embodiment, naturally occurring methanotrophic microorganisms are used to reduce the methane concentration of gaseous emissions.

As discussed previously, methane is an environmentally-destructive material and previously unusable source of energy, which, according to one preferred embodiment of the invention, is used to produce a useful end-product that can be used or sold for use, providing an economic incentive to a methane emissions reduction effort. Although in one embodiment, the harvestable useful end-product is a polymer, another harvestable good is the microorganism culture itself. Thus, in another embodiment, gaseous emissions comprising methane are used to grow a microorganism culture to a density that is capable of being harvested and commercially traded. In sufficient quantities, the microorganism culture can be used, for example, as a nutrition source for livestock. In one embodiment, the end-product is a culture of microorganisms, or the products generated by those microorganisms.

In one embodiment of the invention, methane emissions are processed to produce useful and harvestable products. These products include, but are not limited to: protein-rich biomass, polyhydroxyalkanoate (PHA), polyhydroxybutyrate (PHB), polyhydroxybutyrate-valerate (PHB/V), particulate or soluble methane monooxygenase (pMMO or sMMO, respectively), vaccine derivatives, enzymes, polymers, cellular materials, formaldehyde, and methanol, or a combination thereof. In the commercial and industrial biotechnology art, methanotrophic microorganisms can be manipulated and processed according to several embodiments of the present invention to generate useful, defined, and harvestable goods in sterile, semi-sterile, and non-sterile conditions.

In one embodiment of the invention, a culture of suitable microorganisms is provided for the efficient and effective treatment of methane emissions. The prior art generally criticizes the use of methanotrophic organisms to treat methane emissions, primarily because such a process was thought to be unpredictable, inefficient, and unreliable. For example, the prior art teaches that bioremediation and biofiltration generates a microorganism conglomerate that is non-specific, non-defined, and/or highly variable according to shifts in nutrient availability, air contamination, species interaction, and so on. As emphasized in U.S. Pat. No. 6,599,423, "prior art teaches that ex situ biofilters and bioreactors are akin to microorganism zoos, with the microorganism cultures naturally adapting, dominating, and maintaining themselves according the various compounds, food sources, and contaminants present or fed to the biodegradation media . . . changes, adaptations, and dominance of certain cultures will occur even in such isolated and inoculated cultures after operation begins and the biofilters or bioreactors are subjected to complex mixtures of food sources, contaminants, and microorganisms present in the natural environment." Microbial cultures and the byproducts generated from the growth thereof may be incidentally created in the course of bioremediation, as in the course of any microorganism growth, but, according to the prior art, only in a variable, non-specific, diffuse, unpredictable, speculative, or otherwise non-useful manner. By contrast, in a preferred embodiment of the present invention, a system of using microorganisms in a highly controlled manner for the treatment of gaseous emissions is provided.

The viability and utility of methanotrophic emissions treatment may be augmented by increasing the growth or emissions oxidation rate of methanotrophic microorganisms in order to reduce the capital and operating costs of treatment. While this optimization method renders methanotrophic treatment more efficient, it does not overcome the challenge associated with the continuous generation of non-recoverable costs, and no methods are known in the prior art to optimize the methanotrophic bioremediation process in such a way as to enable practical sustainability. Prior to the applicants' invention, the only methods available for treating methane emissions involved environmental degradation and wasted energy associated with the venting, compression, conversion, and/or combustion of methane emissions.

Prior to the applicants' discovery, it was not recognized that commercial, academic, and/or industrial growth and processing methods known to enable the microbial creation of harvestable products could be applied to overcome previously impassable and fundamental treatment challenges in the field of methane emissions treatment. In particular, it was not known that the use of methanotrophic processes able to engender defined and harvestable bio-based goods, specifically in sterile, semi-sterile, and non-sterile conditions, could be used as a novel methane emissions treatment method to overcome previously impassable practical viability and sustainability challenges. Thus, according to a preferred embodiment of the present invention, a method is provided to enable the practical viability of the biological treatment and utilization of methane emissions. In one embodiment, the method enables the utilization of methane emissions through the production of harvestable goods.

In a preferred embodiment of the inventions, an apparatus or system for processing methane emissions and producing harvestable products is provided. In one embodiment, the system comprises (i) a source of gaseous emissions, wherein the gaseous emissions comprise methane and at least one non-methane compound, (ii) methanotrophic microorganisms that use methane as a source of carbon or energy, (iii) a bioreactor that encloses or contains the methanotrophic microorganisms, and (iv) a conveyer that conveys the gaseous emissions into the bioreactor, thereby exposing the methanotrophic microorganisms to the gaseous emissions and causing the methanotrophic microorganisms to produce a harvestable product after using the methane as a source of carbon or energy.

In accordance with one embodiment of the invention, a novel method for enabling the viable treatment of air containing methane emissions is provided. In one embodiment, methanotrophic microorganisms and air containing methane emissions are mutually-exposed to cause or enable harvestable product formation. The harvestable product may be used or sold. In another embodiment of the invention, air containing methane emissions may be used to create single cell protein, enzymes, polymers, or other bio-based products in a manner that enables product harvest.

In one embodiment, the invention comprises a method of processing methane emissions for the production of a harvestable product, comprising: providing a gaseous emission comprising methane and methanotrophic microorganisms, exposing the methanotrophic microorganisms to the gaseous emission, wherein the methanotrophic microorganisms use at least a portion of the methane as a source of carbon or energy, and wherein the methanotrophic microorganisms produce a harvestable product after using the methane as a source of carbon or energy.

In one embodiment, the harvestable product comprises a polymer (such as polyhydroxyalkanoate (PHA), polyhydroxybutyrate (PHB), and polyhydroxybutyrate-valerate (PHB/V)). In another embodiment, the harvestable product comprises one or more of the following: microorganism biomass, methane monooxygenase, protein-rich biomass, enzymes, and cellular contents. In yet another embodiment, the harvestable product comprises a quantifiable reduction in methane emissions.

In several embodiments, the gaseous emission comprises a gas selected from the group consisting of one ore more of the following: carbon dioxide, ammonia, nitrous oxide, and ozone. In one embodiment, the gaseous emission comprises unpurified landfill gas or partially purified landfill gas. In one embodiment, one or more impurities are removed from the gaseous emission. In another embodiment, the gaseous emission is disinfected using ultraviolet light.

In one embodiment, the invention comprises harvesting the harvestable product for commercial or industrial sale or use.

In one embodiment, the invention comprises substantially reducing or eliminating the concentration of nitrogen available to the methanotrophic microorganisms.

In one embodiment, the invention comprises using gaseous emissions having methane concentrations in the range of about 0.1% to about 10%, in the range of about 10% to about 20%, and at concentrations greater than about 20%. In another embodiment, the methane concentration is less than about 5%. In yet another embodiment, the methane concentration is between about 30% to about 60% of the total gaseous emissions, and carbon dioxide concentration is about 30% to about 60%. The latter numbers are typical of certain landfill emissions.

In one embodiment, the gaseous emission is generated by one or more of the following: coal mine, wastewater treatment operation, agricultural digester, enclosed feedlot, petroleum transport system, and petroleum recovery system. In another embodiment, the gaseous emission is generated by one or more ruminant animals.

In one embodiment, the microorganisms comprise naturally-occurring or genetically-modified microorganisms, or a combination thereof, that use methane as a source of carbon or energy for growth or reproduction. The methanotrophic microorganisms may include one or more of the following: *Methylococcus capsulatus, Alcaligenes acidovorans, Bacillus firmus*, and *Bacillus brevis*.

In a further embodiment, the gaseous emission comprises a non-methane compound, wherein the non-methane compound is an organic compound. In another embodiment, the gaseous emission comprises a non-methane compound such as toluene, benzene, methanol, propylene, alkenes, alcohol, ether, and trichloroethylene, or a combination thereof. Non-methane compounds may also include non-methane gases such as carbon dioxide, ammonia, nitrous oxide, and ozone.

In one embodiment, the non-methane compound is metabolized, consumed, or used by the methanotrophic microorganisms.

In yet another embodiment, the invention comprises reducing the concentration of methane to a concentration compliant with applicable environmental regulations or laws. In the United States, for example, preferred embodiments of the invention reduce methane to concentrations suggested or mandated by local, state, and federal EPA guidelines.

In one embodiment, the present invention comprises a method of producing a biodegradable polymer from landfill gas. In one embodiment, the method comprises obtaining landfill gas, wherein the landfill gas comprises methane, enclosing the landfill gas in a bioreactor containing methanotrophic microorganisms and growth medium, and inducing the methanotrophic microorganisms to produce biodegradable polymer by substantially reducing or depleting the growth medium of any nitrogen. In one embodiment, the method further comprises harvesting the biodegradable polymer.

In one embodiment of the present invention, a system to reduce methane emissions or gaseous emissions comprising methane is provided. In one embodiment, the emissions are produced by land fills, waste processing sites, coal mines, and other similar systems created by humans. In another embodiment, the emissions are produced by ruminant animals.

Thus, in accordance with several embodiments, methane produced through ruminant animal enteric fermentation is used as a source of carbon and/or energy for the induction of a methane-driven process and/or for the production of methane-derived materials, such as methane-utilizing microorganisms, heat, and/or electricity.

In one preferred embodiment, the present invention comprises a system or apparatus for processing methane emissions produced by one or more ruminant animals. In one embodiment, the system comprises (i) one or more ruminant animals that emit gaseous emissions through enteric fermentation, wherein the gaseous emissions comprise methane and at least one non-methane compound, (ii) an enclosure for enclosing the ruminant animals, (iii) a methane-consumption means that uses methane for the production of a product, and (iv) a conveyer that conveys the gaseous emissions to the methane-consumption means, wherein the methane-consumption means is exposed to the methane in the gaseous emissions and uses the methane to generate a harvestable product.

In one embodiment, the present invention comprises a method for processing methane emissions produced by one or more ruminant animals comprising providing one or more ruminant animals that emit gaseous emissions through enteric fermentation. The gaseous emissions comprise methane, airborne materials, and at least one other gas. The method further comprises enclosing the ruminant animals in an enclosure, thereby at least partially enclosing the gaseous emissions. The method also comprises providing a methane-consumption means, or methane consumer, that uses methane to produce a product, and conveying the gaseous emissions to the methane-consumption means. In one embodiment, the method includes causing the methane-consumption means to process the methane to generate a product. The term "causing" is a broad term and includes the act of simply causing methane to come into contact with the methane consumer, and letting nature take its course. In embodiments where engines, turbines or fuel cells are used, the act of causing includes supplying energy to the various components.

In one embodiment, this process of treating gaseous emissions emitted by ruminant animals comprises a) enclosing one or more ruminant animals in an enclosure means, such as a barn, and b) contacting air contained in such an enclosure means, including the enteric fermentation methane contained therein, with a methane-consumption system, whereby enteric fermentation methane emissions are utilized as a novel source of carbon and/or energy for the induction of a methane-based process and/or for the production of methane-based products, such as heat, electricity, and/or methane-utilizing microorganisms.

In a further embodiment, the method of treating ruminant emissions comprises: (a) providing one or more ruminant animals, (b) providing enteric fermentation-derived methane gas that has been emitted by the animals, including air containing the methane, (c) providing means to capture, consolidate, and/or direct the methane, including providing an enclosure means to enclose the animals, the air, and the methane and providing an air conveyor to direct the air and the methane, (d) providing a methane-consumption means which can use the methane as a source of carbon and/or energy in a methane-based process and/or for the production of methane-based goods, and (e) contacting the methane with the methane-consumption means to cause the methane-consumption means to oxidize, consume, and/or otherwise utilize the methane for the operation of a methane-based process or for the production of one or more methane-based products, including methane-utilizing microorganisms, heat, and/or electricity.

In another embodiment, this method comprises: (a) providing one or more ruminant animals, (b) providing an enclosure means to fully or partially enclose and/or otherwise encapsulate the animals, (c) providing enteric fermentation-derived methane gas that has been emitted by the animals, (d) providing enclosure air that has been combined with the methane in the enclosure means, (e) providing a methane-consumption means which can use the methane as a source of carbon and/or energy for the induction of a methane-based process or the production of methane-based goods, (f) providing a means for contacting the air containing the methane with the methane-consumption means, including a means for the conveying the air to the methane-consumption means whereby the methane can be utilized as a source of carbon and/or energy by the methane-consumption means, (g) mutually-contacting and/or exposing the methane and the methane-consumption means to cause the methane-consumption means to oxidize, consume, and/or otherwise utilize the methane for the induction of one or more methane-based processes or for the production of one or more methane-based products, including methane-utilizing microorganisms, heat, and/or electricity, whereby the methane produced by the animals is utilized for the sustained production of the process and/or the products in a specified apparatus.

As discussed previously, methane is an environmentally-destructive material and previously unusable source of energy, which, according to one preferred embodiment of the invention, is used to produce a useful end-product that can be used or sold for use, providing an economic incentive to a ruminant animal methane emissions reduction effort. In one embodiment, the end-product is heat. In another embodiment, the end-product is fuel. In yet another embodiment, the end-product is electricity. In yet another embodiment, the end-product is another form of energy. In a further embodiment, the end-product is the culture of microorganisms.

In one embodiment using ruminant animal emissions, the enclosure means, or enclosure, includes any means by which the animals are fully or partially enclosed or encapsulated. The enclosure includes, but is not limited to, a barn, greenhouse, and/or any other suitable enclosures or housing.

In one embodiment, the term "air" as used herein shall be given its ordinary meaning, and shall include all airborne and gaseous components of air that has been contacted with the methane in the enclosure means, including the methane emitted by the animals contained within the enclosure means, as well as ammonia gas, dust, and/or other airborne materials that may be present in the air.

In one embodiment, methane-consumption means includes any means by which the methane is oxidized, consumed, and/or otherwise used as a form of carbon and/or energy. Methane-consumption means includes, but is not limited to, methane-utilizing microorganisms, fuel cells, turbines, reverse-flow reactors, engines, microturbines, and/or any other methane-consumption means. Accordingly, in some embodiments, methane emissions are conveyed from ruminant animals (or another source) to a fuel cell, turbine, or reactor to produce fuel or other energy. Thus, in some embodiments, methanotrophic microorganisms need not be used.

In one embodiment, the ammonia contained within the air is contacted with liquid water and converted into ammonium and used as a source of nitrogen by the methane-utilizing microorganisms. In one embodiment, the dust and/or other airborne material within the enclosed air is reduced prior to or in the course of using the methane within the air as a source of carbon and/or energy.

In one embodiment, the methane within the air is used by the methane-consumption means in conjunction with alternative sources of methane, such as coal mine methane, landfill gas methane, natural gas methane, manure digester methane, wastewater treatment methane, and/or other sources of methane.

In one embodiment, an air conveyor is provided to direct, move, and/or otherwise convey enclosure air, wherein can be used to contact the air with the methane-consumer. In another embodiment, a conveyer is used to move gaseous and/or methane emissions from one location to another, and may include pipes, tubing, containment means, ducts, channels\and other conduits. In one embodiment, the conveyer is large and/or compartmentalized such that at least a portion of the conveyer serves as the bioreactor, in that it contains methanotrophic organisms.

In one embodiment, the enclosure is erected, modified, and or used to enclose the animals and to make the methane available for use by the methane-consumer. In one embodiment, the enclosure is provided and utilized to collect the air containing the methane.

In one embodiment, the methane emissions provided to the methanotrophic organism or other methane consumption means is provide in conjunction with air, dust, methane, ammonia, gases, insects, particulate matter, and/or other air-borne matter.

In some embodiments, one of skill in the art will appreciate that one or more of the above steps described herein is modified or omitted. Further, the steps need not be conducted in the order set forth herein.

BRIEF DESCRIPTION OF THE DRAWINGS

FIG. 2A is a top cross-sectional view of one of two parts of the apparatus depicted in FIG. 1. The part of the apparatus illustrated is the permanent exhalation conveyance structure that is attached to the body of a ruminant animal.

FIG. 2B is a side perspective view of one of two parts of the apparatus depicted in FIG. 1. The part of the apparatus illustrated is the permanent exhalation conveyance structure that is attached to the body of a ruminant animal.

FIG. 3A is a side cross-sectional view of one of two parts of the apparatus depicted in FIG. 1. The part of the apparatus illustrated is the removable microorganism containment capsule that is inserted into the permanent exhalation conveyance structure.

FIG. 3B is a side perspective view of one of two parts of the apparatus depicted in FIG. 1. The part of the apparatus illustrated is the removable microorganism containment capsule that is inserted into the permanent exhalation conveyance structure.

DETAILED DESCRIPTION OF THE PREFERRED EMBODIMENTS

Figure 1:
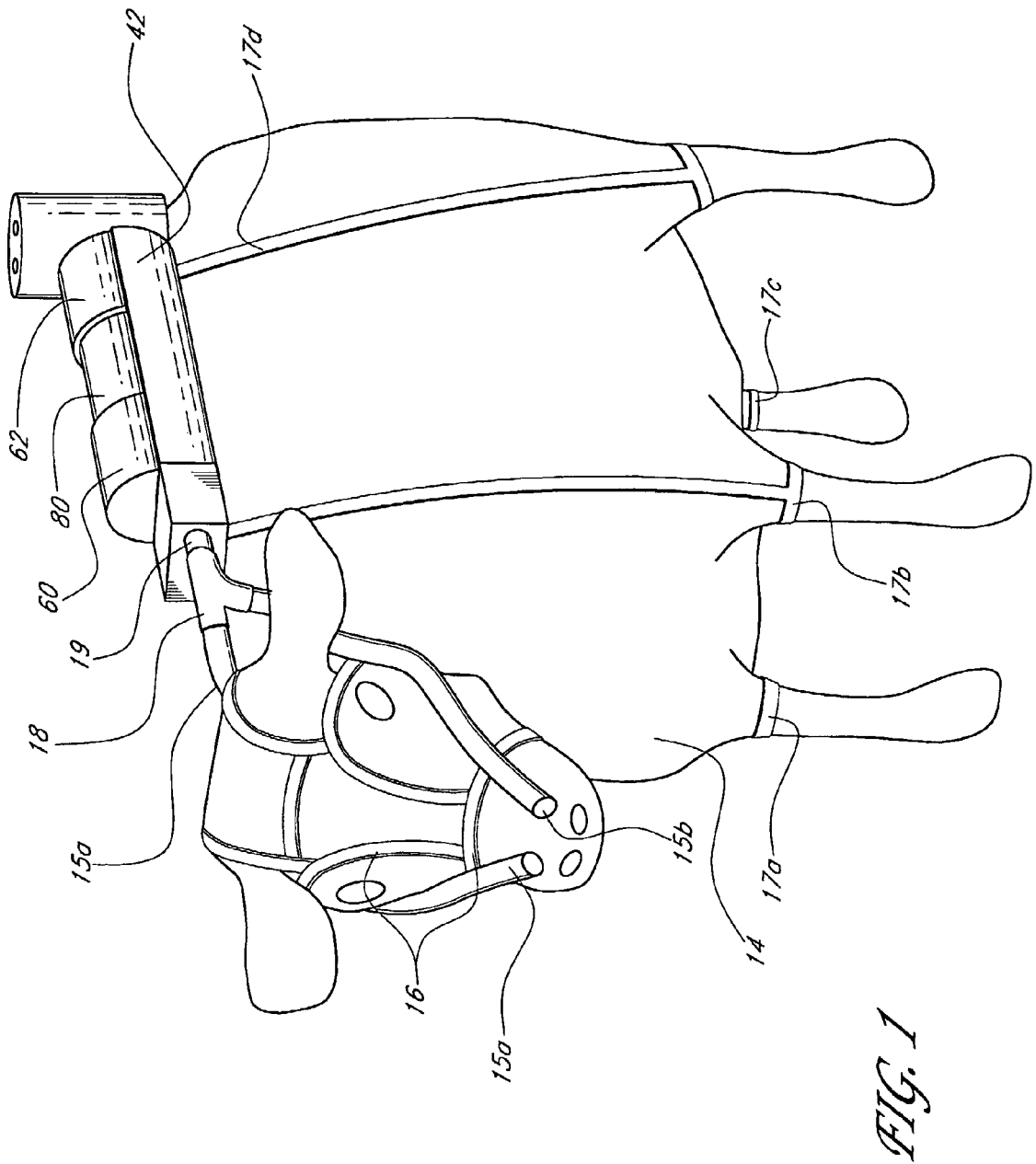
FIG. 1 is a side perspective view of an apparatus used to carry out a process in accordance with one embodiment of the invention. In the illustration, the apparatus is self-contained and maintained entirely on the body of a ruminant animal.

While this invention comprises embodiments in many different forms, there will herein be described in detail preferred methods of carrying out a process in accordance with the invention with the understanding that the present disclosure is to be considered as an exemplification of the principles of the invention and is not intended to limit the broad aspect of the invention to the embodiments illustrated.

In a preferred embodiment of the invention, methane emissions are treated through the use of a product-generating methanotrophic growth system. In one embodiment, this growth system is designed to enable the production of harvestable bio-based goods. For example, in a preferred embodiment, methanotrophic microorganisms and air containing methane emissions are mutually-exposed in an apparatus, such as a bioreactor, filled with methanotrophic bacteria, whereby methanotrophic bacteria use methane emissions for the creation of a harvestable bio-based product.

In one embodiment, the harvestable bio-based product includes, but is not limited to, a polymer such as polyhydroxybutyrate (PHB), single cell protein, enzymes, homogenized biomass, and other harvestable methanotrophic products. This process may be carried out in sterile, semi-sterile, or non-sterile conditions.

The term "harvestable" as used herein shall be given its ordinary meaning and shall also mean usable, producible, collectable, useful, yieldable, and capable of being harvested. Likewise the term "harvest" is a broad term that shall be given its ordinary meaning and shall also mean gather, collect, amass, accumulate, and assemble.

In one embodiment, methane emissions are captured, exposed to, and treated with one or more species of methanotrophic microorganisms to produce a harvestable single cell protein. Single cell protein (or SCP) includes microbial biomass or proteins containing therein or extracted therefrom, and may be used as animal feed, for human nutrition, or for industrial uses. One particularly suitable method for the production of single cell protein is the use of a self-containing conglomerate of microorganisms that promotes product and species stability in non-sterile or semi-sterile conditions. The production process used by Norferm A/S in Norway to create SCP from methane is one example of a methanotrophic growth process that may be applied to carry out one embodiment of the present invention.

Another suitable method for the production of a harvestable product (including, but not limited to SCP) is the use of methods to promote product stability and harvestability. These methods include, but are not limited to: air disinfection, water disinfection, mineral media disinfection, system sterility management, directed species symbiosis, growth conditions management, incoming air gaseous components separation, and others. Accordingly, in one embodiment, product stability and/or harvestability is enhanced or facilitated by one or more of these methods.

In another embodiment of the invention, methane emissions are used to effect the growth of microorganisms, wherein microorganisms are subsequently manipulated to produce harvestable PHB by depriving microorganisms of a particular nutrient, such as nitrogen, on a batch, semi-batch, or continuous basis. Methanotrophic microorganisms (such as *Alcaligenes eutrophus*) employ a polymer (such as PHB) as a form of an energy storage molecule to be metabolized when other common energy sources are not available. Thus, in one embodiment, methanotrophic organisms are periodically or continuously exposed to methane emissions in a nitrogen-poor environment. Partial, substantial, or complete depletion of nitrogen can occur before the organisms are exposed to methane or after such exposure has occurred. Alternatively, nitrogen depletion can occur at some point during exposure of the organisms to methane. As is well known in the art of microbial PHA and PHB production, the depletion of an essential nutrient such as nitrogen in the presence of a sufficient carbon supply will cause bacterial cultures to store energy in the form of PHA, PHB, or, depending on growth conditions, some similar energy storage material, with the aim of accessing this stored energy once all essential growth and reproduction components are fully present at a later time. PHB, or similar energy storage materials, may account for a significant percentage of the weight and/or volume of a single microorganism cell, and may be harvested by any number of well known techniques, such as centrifugation, cell lysis, homogenization, chloroform dissolution, sodium hydroxide dissolution, cell parts extraction, and so on.

In another embodiment of the invention, methanotrophic microorganisms are used to oxidize a quantifiable, monitored, and certifiable volume of methane in a sterile or non-sterile environment, thereby creating a greenhouse gas reduction product which may be "harvested" and sold in a market which purchases and/or trades greenhouse gas reduction credits, such as a carbon dioxide credit trading market. Thus, in one embodiment, the harvestable product is the quantifiable reduction of methane, especially as it pertains to air pollution reductions credits and/or global warming gas emissions reductions credits. Accordingly, in one embodiment of the invention, a system to quantify how much methane has been used is provided. This embodiment will be particularly advantageous for those organizations that need to comply with certain environmental regulations or need to certify that specific volumes of methane have been biologically oxidized.

In another embodiment of the invention, methane emissions may be used to create harvestable enzymes. In one embodiment, the enzyme is methane monooxygenase. In one embodiment, the cell contents may be accessed physically, chemically, enzymatically, or otherwise to enable harvesting in defined or non-defined microbial cultures. The maintenance of copper concentrations will be useful to effect the consistent production of either soluble or particulate methane monooxygenase, as is well known in the art. In particular, if the concentration of copper in a methanotrophic growth medium is minimized and kept below specific and well known concentrations, such as $5 \times 10^{-9}$ M, the production of soluble methane monooxygenase may be effected in most or all methanotrophic cells accessing that copper-limited medium. Soluble or particulate methane monooxygenase may be harvested using any well known methane monooxygenase extraction and purification method.

The processes disclosed herein may be carried out and directed in a controlled bioreactor, wherein liquid, semi-liquid, particulate, or solid mineral media may be used to enhance the growth of methanotrophic microorganisms. Alternatively, the processes described herein may be carried out in reaction tanks, vessels, or other containment systems.

In another aspect of the invention, various processing techniques known in the art may be used to preferentially extract harvestable products of methanotrophic growth, such as chemical treatment, centrifugation, drying, and homogenization.

In a preferred embodiment of the invention, landfill gas is used as the source of methane. In one embodiment, impurities from landfill gas, such as non-methane and/or volatile organic compounds, water vapor, and/or carbon dioxide are partially, substantially, or completely removed. In another embodiment, the landfill gas is disinfected. In one embodiment, UV treatment is used to disinfect the gas. Mechanical, activated carbon, or chemical filtration may also be used.

In one embodiment methane emissions within landfill gas are exposed to methanotrophic microorganisms. In one embodiment, gaseous emissions comprising methane are fed into a bioreactor containing methanotrophic microorganisms suspended in or on a liquid, semi-liquid, or solid growth-culture medium containing water and mineral salts. In another embodiment, after methanotrophic microorganisms have grown and reproduced using methane emissions as a source of carbon and/or energy, these microorganisms are harvested as single cell protein through various extraction and dewatering processes.

In one embodiment, a method of treating gaseous emissions (e.g., landfill gas) is provided. In one embodiment, the method comprises: (i) enclosing the landfill gas in a bioreactor containing methanotrophic microorganisms; and (ii) harvesting the microorganisms and/or the products produced by the microorganisms in the bioreactor. In another embodiment, the method comprises: (i) removing impurities from the landfill gas; (ii) disinfecting the landfill gas; (iii) enclosing the landfill gas in a bioreactor containing methanotrophic microorganisms; and (iv) harvesting the microorganisms and/or the products produced by the microorganisms in the bioreactor.

In one embodiment, a portion of the microorganisms may be directed into a bioreactor containing a nitrogen depleted growth medium and a constant supply of gaseous emissions (e.g., landfill gas), whereby microorganisms synthesize intracellular PHB. In one embodiment, the PHB-filled cells are subsequently removed from the reactor in order to process and harvest intracellular PHB. These processes are preferentially carried out on a continuous, semi-continuous, semi-batch, or batch-wise basis, and methane emissions from any source, including landfills, coal mine, wastewater treatment plants, agricultural systems, or petroleum systems, may be used.

The term "methanotrophic microorganisms" refers to any microorganisms that utilize methane as a source of carbon and/or energy for growth and reproduction, including naturally-occurring and/or genetically engineered microorganisms. It also refers to the combination or mixture of methanotrophic and non-methanotrophic microorganisms that promote the growth of methanotrophic microorganisms. In one preferred embodiment, this combination comprises *Methylococcus capsulatus, Alcaligenes acidovorans, Bacillus firmus*, and *Bacillus brevis*, since this combination has been shown to limit or reduce bacterial contamination in non- and semi-sterile bioreactor conditions, thereby enabling stable product formation. In another preferred embodiment, this combination comprises any methanotrophic microorganisms that may be used to produce polymers such as PHB, enzymes such as methane monooxygenase, and/or any other cellular components. In another preferred embodiment, this combination comprises a non-defined mix of methanotrophic and non-methanotrophic microorganisms that can be used to create a harvestable product from the oxidation (or alternate processing) of methane emissions.

The terms "methanotrophic microorganism growth-culture medium" and "growth medium" refer to any medium promoting the growth of microorganisms, including any one or more of the following: liquid, semi-liquid, gas, particulate, ceramic, foam, plastic, alginate gel, methanol-enriched, copper-enriched, clay, nutrient, or other appropriate growth-culture medium. In a preferred embodiment, this growth culture medium comprises an aqueous solution containing mineral salts, copper, and other trace minerals necessary for the growth and reproduction of methanotrophic bacteria.

In another preferred embodiment, a system comprising methanotrophic organisms is used to degrade or otherwise reduce a pollutant other than methane as a method to enable the viable treatment of methane emissions. In one embodiment, the growth of methanotrophic microorganisms using methane emissions is carried out in the presence of a non-methane material that can be broken-down, oxidized, consumed, and/or otherwise changed in form through the action of such microorganisms, wherein such non-methane material includes, but is not limited to, one or more of the following: toluene, benzene, methanol, propylene, any alkenes, alcohols, ethers, alicyclics, aromatics, and/or chlorinated organic compounds, such as the pollutant TCE, wherein a product, including the oxidized chemical or quantifiable pollutant treatment, may be harvested in a controlled, directed, and/or quantifiable manner.

In another preferred embodiment of the invention, following the growth of methanotrophic microorganisms in a bioreactor, some or all of the contents of the bioreactor are removed from the bioreactor and are either processed or used and sold directly. Processing may include any number of methods that enable product harvest, such as centrifugation, filtration, drying, homogenization, chemical treatment, physical treatment, enzymatic treatment, or any other processing means. Processing means may be used to extract products out of defined or non-defined conglomerates of methanotrophic microorganisms. The application and utilization of processing techniques, such as centrifugation and homogenization, may be used to effect the overall harvestability of the methanotrophic growth and treatment process, especially where the maintenance of a defined culture is unfeasible.

Preferred embodiments of the present invention offer one or more advantages. For example, one or more embodiments provide one or more of the following benefits:

(i) enables the viable and economical utilization of methanotrophic microorganisms in the treatment and utilization of methane emissions;

(ii) enables methanotrophic methane emissions treatment without depending on a reduction in capital or operating costs;

(iii) enables the viable and economical application of methanotrophic microorganisms to methane emissions treatment in environments where a reduction in the concentration of methane emissions is not required;

(iv) provides a methanotrophic methane emissions treatment process that is economically competitive with alternative methods of methane emissions treatment;

(v) provides a process that applies well-known methods of harvestable methanotrophic product-generation as a novel method to enable the sustained treatment and utilization of methane emissions;

(vi) overcomes previously insurmountable practical challenges in the field of methane emissions treatment; and/or (vii) provides a process which, if widely applied, has the capacity to significantly reduce global methane emissions.

Preferred embodiments of the invention comprise one or more of the foregoing advantages and/or objects. Further objects and advantages will become apparent from the ensuing description.

In another preferred embodiment, methane emissions may be used from landfills, coal mines, wastewater treatment plants, manure digesters, agricultural digesters, compost heaps, enclosed agricultural feedlots, leaking or otherwise emitting petroleum systems, and any other source of methane emissions or off-gas whereby the creation of harvestable bio-based is enabled. The methane emitted by ruminant animals can also be used as a source of methane according to several embodiments of the present invention. The processing of methane emissions produced by ruminant animals is discussed below.

Prior to the applicants' discovery, no methods were known to reduce ruminant animal methane emissions by using such methane as a source of energy in energy consumption systems maintained outside of the digestive tracts of ruminant animals. In the past, all ruminant animal methane reduction processes have focused on limiting ruminant animal methane production rather than reducing overall atmospheric emissions through a system of methane utilization. Thus, it is one feature of several embodiments of the present invention that ruminant methane emissions are reduced through the utilization of ruminant animal methane as a source of energy. No methods are believed known to capture and/or consolidate enteric fermentation methane emissions in a way that would convert them into a state suitable for use as a fuel stream for the production of methane-based goods or processes. Enteric fermentation methane originates as diffuse emissions, and no methods are known to convert such emissions into a usable form. For these and other reasons, ruminant animal methane emissions have never been considered as a viable source energy, and the connection between enteric fermentation methane emissions and methane-driven process and goods production has never occurred.

Mechanical ventilation systems are well known in the livestock and agricultural science art for their capacity to draw, push, or pull air through a fully or partially enclosed ruminant animal holding, feeding, or enclosure area. The main function of mechanical ventilation systems, including tunnel ventilation systems and other ventilation systems, is to provide air flow or air exchange in order to maintain or improve the health of ruminant animals in a fully or partially enclosed holding or feeding area. It is also well known in the livestock and agricultural science art that some mechanical ventilation systems, particularly tunnel ventilation systems, have the capacity to force all or some of the air inside a fully or partially enclosed ruminant animal holding or feeding area through specific vents or fans. The outflow air coming out of ventilation fans have even been forced, directed, or led into mulch, compost, and/or other platforms designed to limit or reduce outflow air odor or dust emissions. Prior to the applicants' discovery, though, such ventilation systems used in conjunction with enclosure structures had never been considered as means to enable the capture, consolidation, and utilization of ruminant animal methane emissions as a source of energy. It is one feature of several embodiments of the present invention that animal enclosure structures and/or ventilation systems are applied as means to capture, consolidate, direct, and/or convey ruminant animal methane emissions to enable the use of such emissions as a source of energy. Prior to the applicants' discovery, ventilation systems and/or enclosure structures had never been used to capture ruminant animal enteric fermentation methane emissions, nor had such emissions ever been used to grow bacteria in a bioreactor optionally equipped with means to harvest any of the microbial products associated with bioreactor activity, particularly microbial biomass.

Further, prior to the applicants' discovery, ventilation systems and/or enclosure structures had never been used to capture enteric fermentation methane for utilization by a methane-consumption system such as a reverse-flow reactor or microturbine. The utilization of air conveyance systems to capture enteric fermentation methane for use as a source of carbon and/or energy overcomes a range of practical problems associated with a system for capturing methane emissions from the nose and/or mouth of a ruminant animal using on-animal apparatuses such as bioreactors or microturbines, including animal mobility problems and reactor size requirements for optimal methane conversion. The straightforward utilization of structures, means, and systems that are well known and/or commonly used also overcomes a range of prior emissions capture problems, including practicability, palatability, and viability. One of skill in the art will understand that currently available and other ventilation systems can be used in accordance with embodiments of the invention.

As described herein, several embodiments of the present invention provide a novel process for the utilization of methane emitted by ruminant animals. Preferred embodiments of the invention involving ruminant animal emissions are particularly advantageous because they provide one or more of the following benefits:

(i) converts a previously wasted form of energy into a useful end-product, (ii) converts an environmentally-destructive greenhouse gas into a useful end-product, (iii) provides a direct economic incentive for a ruminant animal methane emissions reduction effort, (iv) reduces atmospheric ruminant animal methane emissions without altering the chemical or microbial make-up of the digestive tract of ruminant animals, (v) reduces atmospheric ruminant animal methane emissions without requiring ruminant animals to alter their normal/natural behavior patterns, including sleeping and nutrient-consumption, (vi) reduces atmospheric ruminant animal methane emissions without requiring feed reformulations, selective breeding activities, or chemical or microbial modifications to the digestive systems of ruminant animals, (vii) utilizes as a source of energy a material never previously considered a viable source of energy, and/or (viii) has the potential, especially if used widely, to significantly reduce ruminant animal methane emissions.

As used herein, the terms "ruminant animal methane", "enteric fermentation methane", and "ruminant animal enteric fermentation methane" shall be given their ordinary meaning and shall also refer to any methane produced and emitted by one or more ruminant animals as a result of processes associated with enteric fermentation. An average adult dairy cow will emit approximately 150 kg of enteric fermentation methane per year, while beef cattle will each produce about two-thirds of that volume, or 100 kg per year. Methane emitted by ruminant animals is a particularly important greenhouse gas, since on a ton-to-ton basis it has 21 to 23 times the heat-trapping capacity of carbon dioxide.

The term "consolidation means" shall be given its ordinary meaning and shall also refer to any means by which enclosure air is unified, mutually-directed, and/or otherwise consolidated for conveyance. In one preferred embodiment, a consolidation means comprises an air-tight ducting tube running from an air outlet to a mutual-exposure means, as described below, wherein enclosure air is directed out of an enclosed area, through a consolidation means, and into a mutual-exposure means. In another preferred embodiment, a consolidation means comprises multiple ducting tubes connected to air outlets and situated to consolidate outflowing enclosure air into a single ducting tube that ultimately leads as one or more air streams into a methane-consumption system.

The term "ventilation means" shall be given its ordinary meaning and shall also refer to any means by which air, gases, and/or other airborne material is mechanically forced, pushed, pulled, drawn, moved, conveyed, or otherwise directed into, through, and/or out of a spatial area enclosed by an enclosure means. In one preferred embodiment, well-known ventilation fans, such as rotating ventilation fans and/or tunnel ventilation fans, operate in a well-known barn ventilation process, whereby air may be drawn into a barn through one or more open spaces in a barn wall and directed out of a barn through ventilation fans. In one preferred embodiment, an enclosure means is provided with ventilation means, wherein air is moved into and out of an enclosure means at an overall combined rate of 10 cubic feet per minute per dairy cow. In one preferred embodiment, means for the cooling of barn-enclosed air are also provided in order to ensure animal well-being in an enclosed area. A number of air-cooling means are well known, such as cooling pads, water sprayers, and air conditioning units.

The term "ruminant animal" shall be given its ordinary meaning and shall also refer to one or more ruminant animals, including, as in one preferred embodiment, a dairy or beef cow.

The terms "enclosure means" and "means for enclosure" shall be given their ordinary meaning and shall also refer to any means by which some or all of the space in which one or more ruminant animals exist is partially or fully confined, isolated, encapsulated, and/or enclosed, such as a barn or greenhouse structure. In one preferred embodiment, a barn with a specified air inlet, such as a window, and a specified air outlet, such as a window housing a ventilation fan, encloses a ruminant animal (e.g., dairy cow).

The term "air inlet" shall be given its ordinary meaning and shall also refer to any location where air, gas, and/or other airborne material enters into an area or chamber fully or partially enclosed by an enclosure means. In one preferred embodiment, an air inlet comprises a spatial opening, such as a window, in the wall of an enclosure means.

The term "air outlet" shall be given its ordinary meaning and shall also refer to any location where air, gas, and/or other airborne material exits out an area or chamber fully or partially enclosed by an enclosure means. In one preferred embodiment, an air outlet comprises a spatial opening housing a ventilation means located in the wall of an enclosure means.

The term "enclosure air" shall be given its ordinary meaning and shall also refer to the air, gases, and/or other airborne material that have been mixed with enteric fermentation methane in the space fully or partially enclosed by an enclosure means, including enteric fermentation methane, ammonia, dust, and/or other airborne material contained within an enclosure means containing a ruminant animal.

Methane-utilizing microorganisms represent one embodiment of a "methane-consumption system" or "methane consumption means." The latter two terms include a biological system that utilizes enteric fermentation methane as a source of carbon and/or energy, a mechanical system that uses or consumes methane, and/or a chemical system that uses, degrades, consumes, or reacts with methane.

The term "methane-utilizing microorganism" or "methanotrophic microorganism" shall be used interchangeably, shall be given their ordinary meaning, and shall also refer to any microorganism, naturally-occurring or genetically-engineered, that utilizes methane, including enteric fermentation methane, as a source of carbon and/or energy. The term "methane-utilizing microorganisms" also refers to the combination of methane-utilizing and non-methane-utilizing microorganisms that are collectively associated with the growth of methane-utilizing microorganisms. In one embodiment, this microorganism combination includes one or more of the following: *Methylococcus capsulatus, Alcaligenes acidovorans, Bacillus firmus,* and *Bacillus brevis*. In one embodiment, a combination of these microorganisms is used because among other advantages, this combination is known to promote the long-term growth of *Methylococcus capsulatus*. The term "methane-utilizing microorganisms" also includes any methanotrophic organisms and organisms that use or "take-up" methane. Methane-utilizing microorganisms may be confined in a microorganism holding tank containing methane-utilizing microorganisms and a microorganism growth-culture medium. They may also be present in a biofiltration system containing methane-utilizing microorganisms wherein microorganisms either are or are not attached to a microorganism support substrate and are continuously or intermittently contacted with a microorganism growth-culture medium. They may also be used in a bioreactor containing methane-utilizing microorganisms and a microorganism growth-culture medium wherein the growth-culture medium is in liquid, foam, solid, semi-solid, or any other suitable form and methane-utilizing microorganisms are naturally-occurring and/or genetically engineered and may or may not have been selectively inserted as part of a pre-determined microbial consortium. While the use of specified microorganism consortium may provide some benefits, a non-specified and naturally-equilibrating consortium of one or more microorganisms may also be employed. Typical examples of methane-utilizing microorganisms useful in several embodiments of the present invention include, but are not limited to, bacteria and yeast.

Suitable yeasts include species from the genera *Candida, Hansenula, Torulopsis, Saccharomyces, Pichia,* 1-*Debaryomyces, Lipomyces, Cryptococcus, Nematospora,* and *Brettanomyces*. The preferred genera include *Candida, Hansenula, Torulopsis, Pichia,* and *Saccharomyces*. Examples of suitable species include: *Candida boidinii, Candida mycoderma, Candida utilis, Candida stellatoidea, Candida robusta, Candida claussenii, Candida rugosa, Brettanomyces petrophilium, Hansenula minuta, Hansenula saturnus, Hansenula californica, Hansenula mrakii, Hansenula silvicola, Hansenula polymorpha, Hansenula wickerhamii, Hansenula capsulata, Hansenula glucozyma, Hansenula henricii, Hansenula nonfermentans, Hansenula philodendra, Torulopsis candida, Torulopsis bolmii, Torulopsis versatilis, Torulopsis glabrata, Torulopsis molishiana, Torulopsis nemodendra, Torulopsis nitratophila, Torulopsis pinus, Pichia farinosa, Pichia polymorpha, Pichia membranaefaciens, Pichia pinus, Pichia pastoris, Pichia trehalophila, Saccharomyces cerevisiae, Saccharomyces fragilis, Saccharomyces rosei, Saccharomyces acidifaciens, Saccharomyces elegans, Saccharomyces rouxii, Saccharomyces lactis,* and/or *Saccharomyces fractum*.

Suitable bacteria include species from the genera *Bacillus, Mycobacterium, Actinomyces, Nocardia, Pseudomonas, Methanomonas, Protaminobacter, Methylococcus, Arthrobacter, Methylomonas, Brevibacterium, Acetobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus,* and *Methylocystis*. Preferred genera include *Bacillus, Pseudomonas, Protaminobacter, Micrococcus, Arthrobacter* and/or *Corynebacterium*. Examples of suitable species include: *Bacillus subtilus, Bacillus cereus, Bacillus aureus, Bacillus acidi, Bacillus urici, Bacillus coagulans, Bacillus mycoides, Bacillus circulans, Bacillus megaterium, Bacillus licheniformis, Pseudomonas ligustri, Pseudomonas orvilla, Pseudomonas methanica, Pseudomonas fluorescens, Pseudomonas aeruginosa, Pseudomonas oleovorans, Pseudomonas putida, Pseudomonas boreopolis, Pseudomonas pyocyanea, Pseudomonas methylphilus, Pseudomonas brevis, Pseudomonas acidovorans, Pseudomonas methanoloxidans, Pseudomonas aerogenes, Protaminobacter ruber, Corynebacterium simplex, Corynebacterium hydrocarbooxydans, Corynebacterium alkanum, Corynebacterium oleophilus, Corynebacterium hydrocarboclastus, Corynebacterium glutamicum, Corynebacterium viscosus, Corynebacterium dioxydans, Corynebacterium alkanum, Micrococcus cerificans, Micrococcus rhodius, Arthrobacter rufescens, Arthrobacter parafficum, Arthrobacter citreus, Methanomonas methanica, Methanomonas methanooxidans, Methylomonas agile, Methylomonas albus, Methylomonas rubrum, Methylomonas methanolica, Mycobacterium rhodochrous, Mycobacterium phlei, Mycobacterium brevicale, Nocardia salmonicolor, Nocardia minimus, Nocardia corallina, Nocardia butanica, Rhodopseudomonas capsulatus, Microbacterium ammoniaphilum, Archromobacter coagulans, Brevibacterium butanicum, Brevibacterium roseum, Brevibacterium flavum, Brevibacterium lactofermentum, Brevibacterium paraffinolyticum, Brevibacterium ketoglutamicum,* and/or *Brevibacterium insectiphilium*.

The term "microorganism growth-culture medium" shall be given its ordinary meaning and shall also refer to any medium promoting the growth of microorganisms. It shall also refer to any substrate, aside from methane, which microorganisms oxidize or otherwise break down. It shall also refer to any substrate or material that concentrates methane, preferentially sequesters methane, "traps" methane, increases the solubility and/or availability of methane, and/or otherwise enables the enhanced breakdown, oxidation, and/or utilization of methane by microorganisms. The term "microorganism growth-culture medium" includes, but is not limited to, any substrate and/or microorganism immobilization means, such as liquid, semi-liquid, gas, particulate, ceramic, foam, plastic, alginate gel, methanol-enriched, copper-enriched, clay, nutrient, or other appropriate growth-culture medium. In one preferred embodiment, this growth culture medium comprises aqueous solution containing water, nitrogen, ammonium, trace minerals, and other well-known microorganism growth-culture medium components necessary for the growth and reproduction of methane-utilizing bacteria. In another preferred embodiment, this growth culture medium comprises a microorganism immobilization means, such as organic or inorganic particles, on which a liquid or semi-liquid mineral medium solution is continuously or periodically contacted and on which microorganisms are attached. In another preferred embodiment, this growth-culture medium comprises waste organic materials, which methane-utilizing microorganisms may or may not break down to produce a byproduct of organic materials that may or may not be useful. In another preferred embodiment, this growth-culture medium comprises a liquid foam substrate.

In yet another preferred embodiment, the growth-culture medium is combined with various materials which methane-utilizing microorganisms may or may not convert to more desirable materials. Examples of various materials include, but are not limited to, toluene, trichloroethylene (TCE), propylene, and agricultural byproduct materials which microorganisms may preferentially breakdown or oxidize.

In one embodiment, the invention comprises conveying enteric fermentation methane to an apparatus situated entirely on the body of a ruminant animal which mutually-exposes methane-utilizing microorganisms, enteric fermentation methane, and a microorganism growth-culture medium, causing methane-utilizing microorganisms to grow using enteric fermentation methane as a source of carbon and/or energy. Preferred embodiments of the invention are described below and illustrated by FIGS. 1, 2, and 3.

FIG. 1 is a side perspective view of an apparatus used to carry out a process in accordance with the invention. In this illustration, all of the means necessary for carrying out a process in accordance with the invention are maintained and situated entirely on the body of ruminant animal, including means for conveying ruminant animal exhalation, and the exhalation methane therein, to a means for mutually-exposing enteric fermentation methane, methane-utilizing microorganisms, and a microorganism growth-culture medium, as well as a means for harvesting the product of methane-utilizing microorganism growth. In other embodiments, one or more components are not located on the animal, but instead are coupled to or in communication with the animal.

In FIG. 1, exhalation collection tubes 15a and 15b are situated one on either side of the head of ruminant animal 14. Tubes 15a and 15b are held in place by stationary head harness 16 and lead up to the nostrils of ruminant animal 14. Tubes 15a and 15b run from the nostrils of ruminant animal 14 to where they both converge into exhalation collection tube convergence T-pipe 18. T-pipe 18 connects to exhalation inflow tube 19, which leads to permanent exhalation conveyance structure 20. Structure 20 is described in further detail by FIGS. 2A and 2B. Structure 20 is held in place on the back of ruminant animal 14 by stabilizing leg straps 17a, 17b, 17c, and 17d, as illustrated.

Figure 2A:
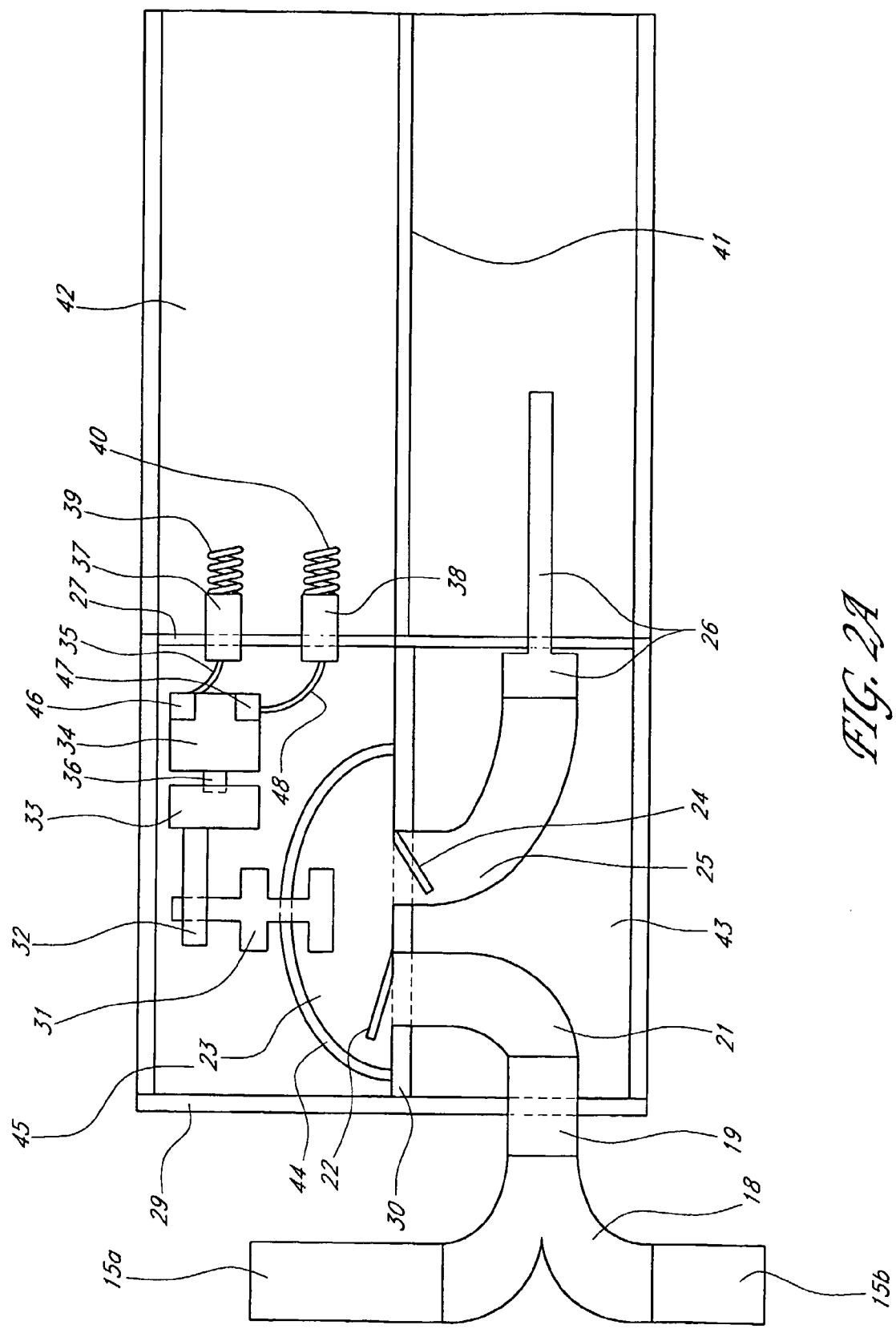
FIGS. 2A, 2B, 3A, and 3B describe this apparatus in greater detail.
Figure 2B:
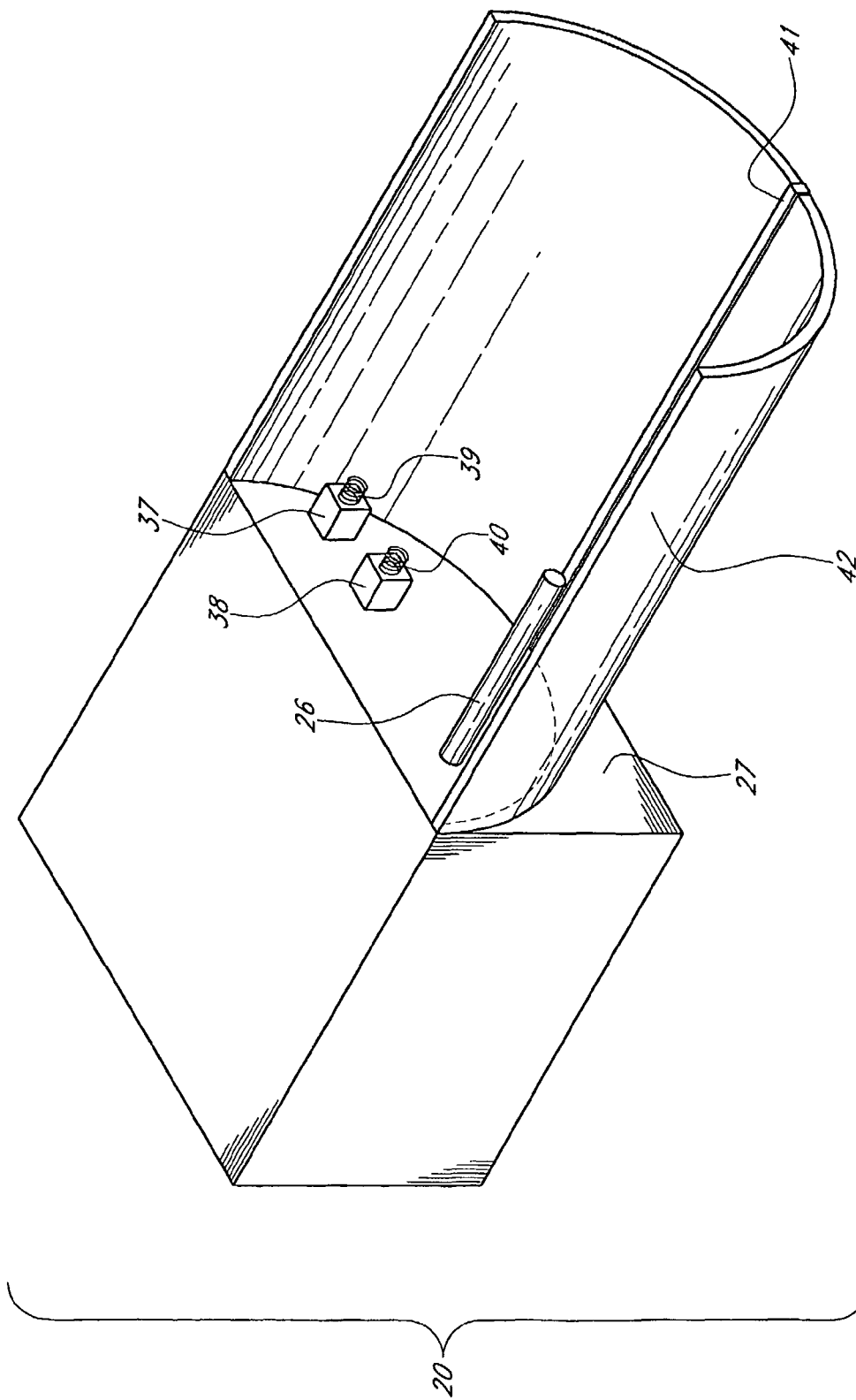

FIG. 2A is a top cross-sectional view of structure 20, and FIG. 2B is a side perspective view of structure 20. Tube 19 passes through air pump housing front wall 29 and leads into exhalation flow pipe chamber 43. Inside chamber 43, tube 19 connects to inflow pump chamber tube 21, which leads through chamber 43, through air pump housing middle wall 30, and into diaphragm-enclosed chamber 23. Where tube 21 opens into chamber 23 is inflow one-way flap sphincter 22, which, being a one-way flap, allows air to travel into chamber 23, but does not allow air to travel from chamber 23 into tube 21.

Chamber 23 is enclosed by rubber diaphragm 44. The open end of diaphragm 44 is attached to wall 30 so that an air-tight seal is made, and chamber 23 is formed. Diaphragm pump plunger 31 is inserted through and into diaphragm 44 on the side of diaphragm 44 farthest from wall 30. Plunger 31 extends out of diaphragm 44 to where it is joined perpendicularly to rotational gear tooth 32, which is attached to rotational gear 33. Gear 33 is mounted on motor axle 36, which leads into direct-current rotational motor 34. Motor 34 is located inside exhalation motor pumping chamber 45. Positive motor electrical terminal 46 is connected to permanent structure positive conduction plate 37 by positive electrical conduction wire 35. Negative motor electrical terminal 47 is connected to permanent structure negative conduction plate 38 by negative electrical conduction wire 48. Plate 37 and plate 38 are mounted on air pump housing back wall 27 with portions of each plate protruding through and outside of wall 27. Connected to the end of plate 37 on the end farthest from chamber 45 is positive conduction continuation spring 39. Connected to the end of permanent structure negative conduction plate 38 on the end farthest from chamber 45 is negative continuation spring 40. Structurally, an electric current can now flow from spring 39 to terminal 46 as well as from spring 40 to terminal 47.

Returning to chamber 23, outflow one-way flap sphincter 24 leads out from chamber 23 and into outflow pump chamber tube 25. Sphincter 24 allows air to travel out of chamber 23, but it does not allow air to travel from tube 25 into chamber 23. Tube 25 runs from chamber 23, through wall 30, and through chamber 43 to where it finally connects with outflow insertion needle 26. Needle 26 runs from the inside of chamber 43, protrudes through wall 27, and extends beyond wall 27 directly away from tube 19. Needle 26 is open on the end farthest from tube 25.

Half-cylindrical shell 42 is attached to wall 27. The orientation of shell 42 is depicted in FIG. 2B. Running the length of shell 42 is inlaid guidance groove 41. As will be described later, groove 41 has the purpose of guiding removable microorganism containment capsule 99 into correct orientation with needle 26, spring 39, and spring 40. Capsule 99 is described in greater detail in FIGS. 3A and 3B.

Figure 3A:
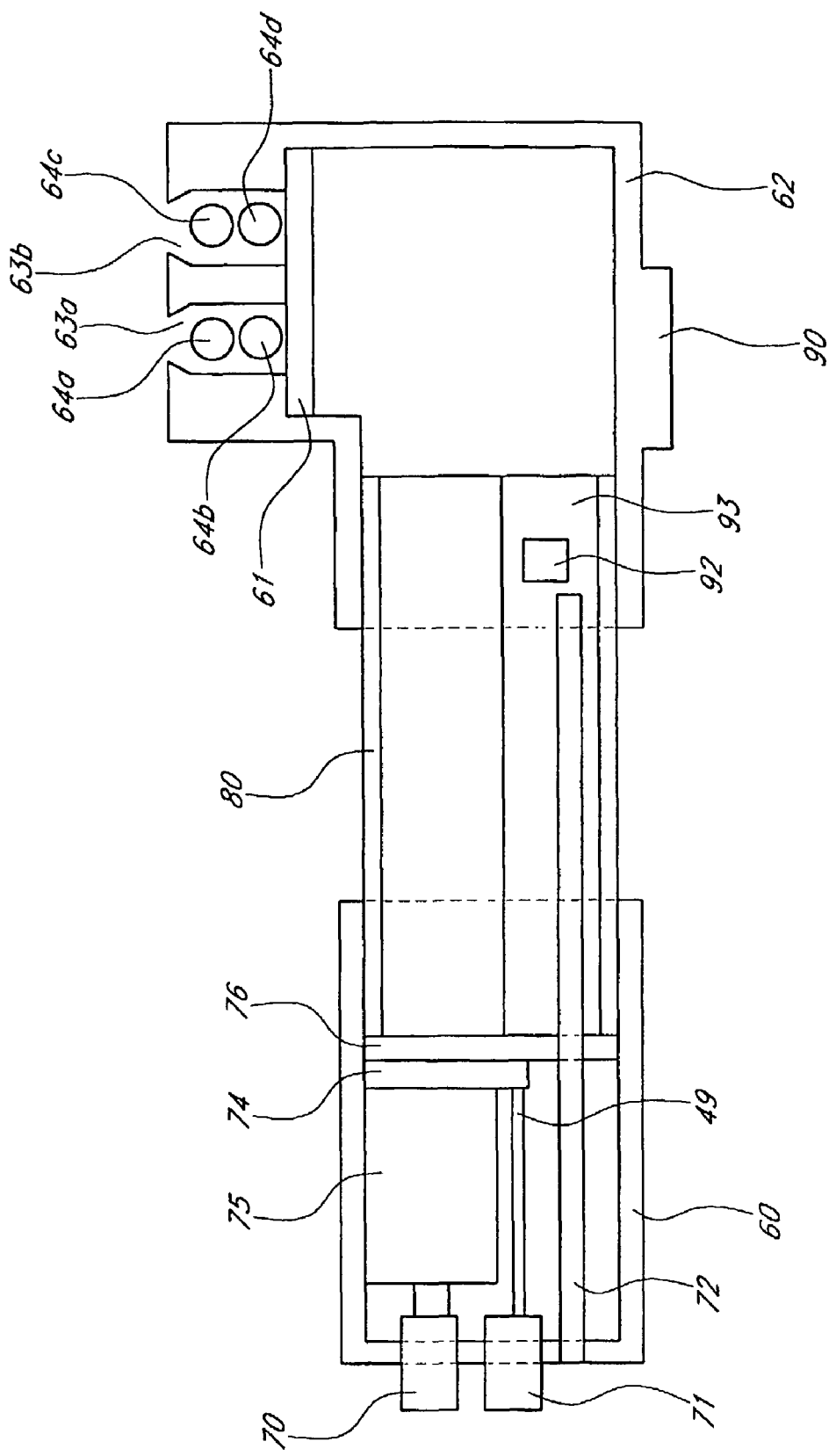
Figure 3B:
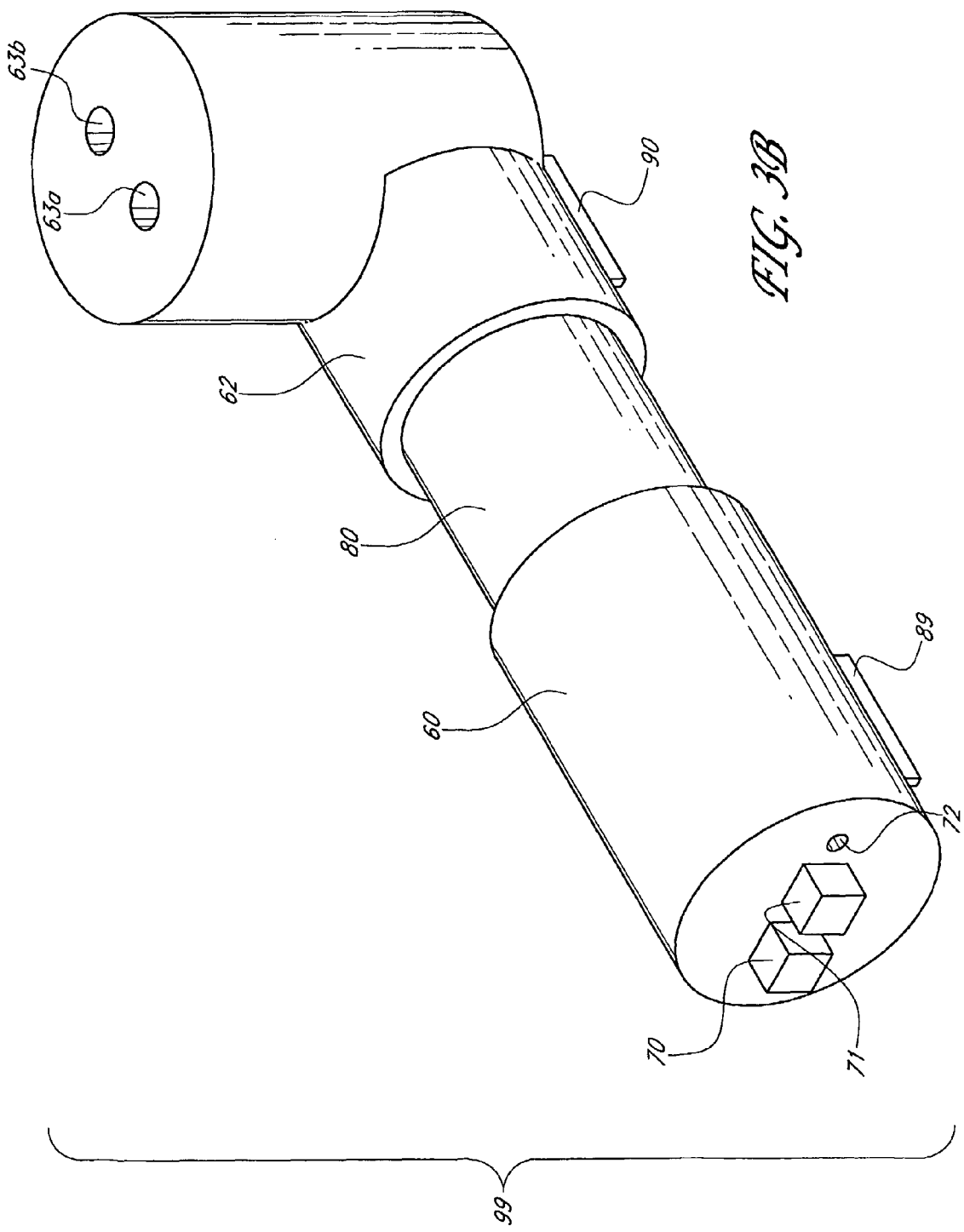

FIG. 3A and FIG. 3B depict capsule 99. Specifically, FIG. 3A is a side cross-sectional view of capsule 99, and FIG. 3B is a side perspective view of capsule 99. Structure 20 is designed to support and feed ruminant animal exhalation (and the methane contained therein) into capsule 99. Designed accordingly, capsule 99 is described in three parts: threaded inflow attachment pipe 60, threaded outflow attachment pipe 62, and microorganism growth capsule pipe 80. Capsule 99, as a whole, consists of each of these three pieces connected together, as will be described.

Pipe 80 is threaded on the outer side of both ends and contains methane-utilizing microorganisms 92 and microorganism growth-culture medium 93. In the present embodiment, 5 grams of *Methylococcus capsulatus*, methane-utilizing microorganisms which can be obtained from a number of biological supply depots (including Chang Bioscience, located at 125 Cambon Drive #6H, San Francisco, Calif. 94132) are placed in an aqueous microorganism growth-culture medium containing ammonium, nitrogen, and mineral salts.

Attached to one end of pipe 80 is pipe 60. Attached on the other end of pipe 80 is pipe 62. Pipe 60 houses D-size battery 75, which is situated between removable capsule positive electrical conduction terminal 70, removable capsule negative electrical conduction plate 74, and inflow attachment pipe inner wall 76. Plate 74 rests against wall 76 and sits adjacent to battery 75. Terminal 70 sits adjacent to battery 75 and protrudes through the front side of pipe 60. Similarly, terminal 71 protrudes through the front side of pipe 60 from the inside of pipe 60. Capsule negative electrical conduction wire 49 runs from terminal 71 to plate 74. Running from the outer edge of the front side of pipe 60, passing through wall 76, and extending beyond wall 76 into pipe 80 is air dispersion capillary tube 72. Tube 72 is a solid tube except for the portion extending into pipe 80, which contains tiny capillary holes in its walls that allow air to pass out of tube 72 but do not allow medium 93 to pass into tube 72. Tube 72 is open at the end meeting the outer edge of the front side of pipe 60, and closed at its opposite end. Attached to the outside of pipe 60 is inflow guidance ridge 89, a solid piece of material which will eventually fit into groove 41 illustrated in FIG. 2A and FIG. 2B.

Attached to pipe 80 on the end opposite pipe 60 is pipe 62. Pipe 62 is an elbow-shaped pipe that allows air to escape after it has passed through the small holes in the walls of tube 72. Pipe 62 is a hollow piece of piece of pipe at the end where it is connected to pipe 80, though, at its other end, pipe 62 is a solid piece of pipe. Wire mesh grating 61 is located inside pipe 62 at the border of where pipe 62 turns from hollow to solid. Still inside of pipe 62, adjacent to grating 61 in the solid portion of pipe 62, leak prevention holes 63*a* and 63*b* are drilled through the solid piece of pipe 62. Inside of hole 63*a* are plug balls 64*a* and 64*b*. Inside of hole 63*b* are plug balls 64*c* and 64*d*. Balls 64*a*, 64*b*, 64*c*, and 64*d* are rubber balls which can float on the surface of medium 93. Holes 63*a* and 63*b* are partially blocked at both the ends farthest and the ends closest to the hollow portion of pipe 62. Holes 63*a* and 63*b* are partially blocked by grating 61 at the end closest to the hollow portion of pipe 62. While the diameters of holes 63*a* and 63*b* are constant throughout, the diameters decrease at the ends farthest from the hollow portion of pipe 62 such that a single ball (64*a* or 64*c*) cannot pass through that end. Similar to ridge 89, outflow guidance ridge 90, which is able to slide into groove 41, is located on the outside of pipe 62.

The following is a description of one method by which an apparatus is used to carry out a process in accordance with one embodiment of the invention.

First, structure 20 is situated on the back of ruminant animal 14 using straps 17*a*, 17*b*, 17*c*, and 17*d*. Next, harness 16 is attached to the head of ruminant animal 14, and tubes 15*a* and 15*b* are connected to harness 16 such that tubes 15*a* and 15*b* lead from T-pipe 18 up to the nostrils of ruminant animal 14.

Second, capsule 99 is placed into shell 42 of structure 20. This is accomplished by inserting ridge 89 and ridge 90 on capsule 99 into groove 41 inlaid in shell 42 of structure 20. With capsule 99 aligned with structure 20, capsule 99 is slid towards wall 27 up to the point where needle 26 is inserted into tube 72, and spring 39 and spring 40 are placed, respectively, into contact with terminal 70 and terminal 71. With terminal 70 and terminal 71 placed into contact with spring 39 and spring 40, respectively, an electrical current now runs from battery 75 in capsule 99 to motor 34 in structure 20. Specifically, a positive electrical current runs from battery 75, through terminal 70, through spring 39, through plate 37, though wire 35, to terminal 46. A negative electrical current runs from battery 75, through plate 74, through wire 49, through terminal 71, through spring 40, through plate 38, through wire 48, to terminal 47.

With an electrical current running from battery 75 to motor 34, axle 36 on motor 34 begins to rotate rapidly. As axle 36 rotates, gear 33 and gear tooth 32 also rotate rapidly, which in turn causes plunger 31 to rapidly push and pull diaphragm 44. With diaphragm 44 oscillating towards and away from wall 30, the motion of diaphragm 44 causes air to flow from tubes 15*a* and 15*b*, into chamber 23, and into needle 26. To expand, air is pulled through tubes 15*a* and 15*b*, through T-pipe 18, through tube 19, through tube 21, past sphincter 22, through chamber 23, past sphincter 24, through tube 25, and into needle 26.

With capsule 99 inserted, as described above, into structure 20, air now travels from needle 26 into tube 72. Since tube 72 is blocked at the end located in pipe 80 and since air cannot travel from tube 72 back into chamber 23, air is forced out through the tiny holes which exist in the walls of tube 72. To reiterate a detail mentioned above, in one embodiment, tiny holes exist in the walls of tube 72 only where tube 72 extends into pipe 80. The result is that air is conveyed from needle 26, through tube 72, and into pipe 80. Eventually, with no other means of escape, the air inside pipe 80 flows into the hollow portion of pipe 62, past grating 61, into holes 63*a* and 63*b*, past plug balls 64*a*, 64*b*, 64*c*, and 64*d*, out of holes 63*a* and 63*b*.

The result of this conveyance of air is that as ruminant animal 14 exhales, this exhalation, as well as exhalation methane therein, is conveyed and directed into tubes 15*a* and 15*b*, which are situated just above the nostrils of ruminant animal 14. Exhalation methane now travels through tubes 15*a* and 15*b* to needle 26. With capsule 99 inserted, as described above, into structure 20, exhalation methane of ruminant animal 14 travels through needle 26 into pipe 80.

Pipe 80 contains microorganisms 92 and medium 93, and when exhalation methane is conveyed into pipe 80, microorganisms 92 grow and reproduce using this exhalation methane as a source of carbon and/or energy. Put differently, exhalation methane, microorganisms 92, and medium 93 are mutually-exposed in pipe 80. Thus, as more exhalation methane from ruminant animal 14 is exposed to microorganisms 92 in medium 93, microorganisms 92 grow and reproduce using exhalation methane as a source of carbon and/or energy. All excess gases, including waste carbon dioxide and waste exhalation methane, exit capsule 99 as described above.

Although medium 93 is an aqueous medium, holes 63*a* and 63*b*, balls 64*a*, 64*b*, 64*c*, and 64*d*, and grating 61 act together to prevent medium 93 from spilling or escaping out of capsule 99. Specifically, since plug balls 64*a*, 64*b*, 64*c*, and 64*d* are designed to float on the surface of medium 93, if medium 93 travels past grating 61 and moves into holes 63*a* and/or 63*b*, balls 64*a* and 64*c* will plug the small-diameter end of holes 63*a* and 63*b*, respectively, before the aqueous medium 93 can pass out of capsule 99.

The process continues when, after a certain amount of time (in this embodiment approximately 7 days) it is determined that microorganisms 92 within capsule 99 are no longer growing at optimal rates or have stopped growing completely, and capsule 99 is removed from structure 20. The microorganism growth process is re-started and continued simply by replacing previously-used capsule 99 with a new apparatus structurally identical to capsule 99 containing new methane-utilizing microorganisms and a new microorganism growth-culture medium. The process may also be continued by re-using capsule 99 and, after removing all or most of microorganisms 92 and medium 93, filling it with new microorganism growth-culture medium and an optimal number of new or previously used methane-utilizing microorganisms. In such a manner, exhalation methane is continually used as a source of carbon and/or energy for the growth and harvesting of methane-utilizing microorganisms.

Finally, microorganisms 92, having been grown in capsule 99 using exhalation methane as a source of carbon and/or energy, are removed from capsule 99 and harvested as useful biomass. (*Methylococcus capsulatus* has a biomass which consists of about seventy percent protein by weight). Such biomass can be processed and sold as a nutritional foodstuff or converted into other useful products, such as adhesives or cosmetics.

Figure 4:
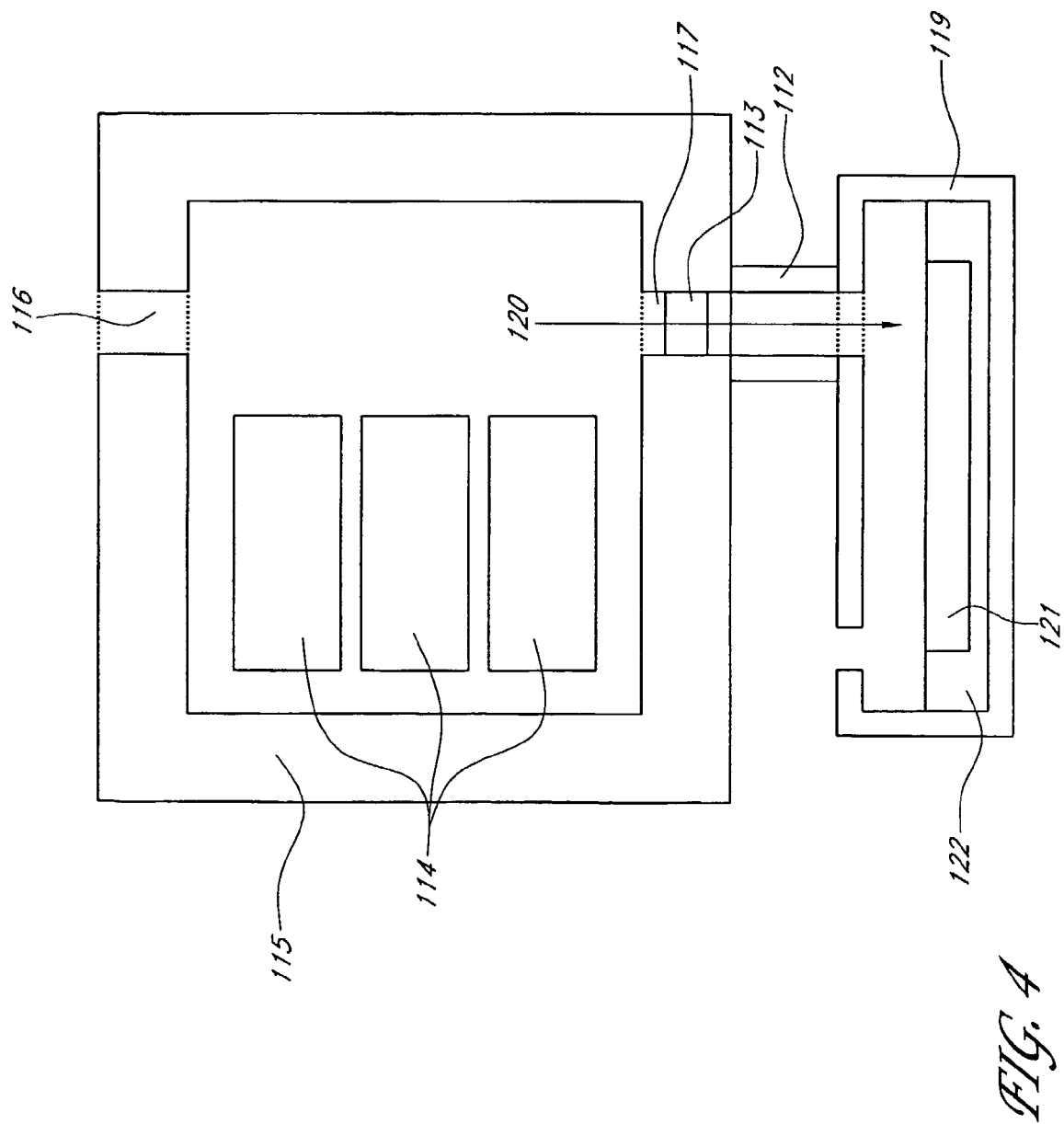
FIG. 4 is a schematic of a preferred embodiment of a process carried out in accordance with one embodiment of the invention.

In one preferred embodiment, as detailed by FIG. 4, "mutual-exposure means" shall be given its ordinary meaning and shall also refer to any apparatus housing, holding, or containing a methane-consumption system such as microorganisms, fuel cells, or microturbines. In one embodiment, this apparatus comprises a holding tank containing methane-utilizing microorganisms and a microorganism growth-culture medium. In another embodiment, this apparatus comprises the materials housing and/or supporting the operation of a reverse-flow reactor, an engine, a fuel cell, and/or a microturbine. In another embodiment, this means comprises a temperature-controlled, stainless-steel cylindrical bioreactor apparatus containing, holding, or enclosing methanotrophic microorganism growth-culture medium and methane-utilizing microorganisms, into which enclosure air, including ammonia and ruminant animal methane, is fed, conveyed, or directed, which subsequently allows microorganisms to grow and reproduce utilizing ruminant animal methane as a source of carbon and/or energy for growth. In another embodiment, the growth of random, non-specified, genetically-engineered, pre-determined, and/or non-pre-determined methane-utilizing microorganisms in such a bioreactor may be used to lower the concentration of ammonia in enclosure air. In another embodiment, means are provided to trap or capture dust and other airborne matter in the enclosure air such that any or all of such matter does not actually contact a methane-consumption means, such as methane-utilizing microorganisms or a methane-driven microturbine, reverse-flow reactor, or fuel cell. In this way, a mutual-exposure means may be used not only to carry out methane-driven processes, but also to lower the dust, ammonia, and/or airborne matter contents in enclosure air.

Several embodiments of the subject invention pertain to the utilization of the enteric fermentation methane produced by ruminant animals for the production of methane-based goods. More particularly, some embodiments of the present invention pertain to the process of utilizing ruminant animal enteric fermentation methane emissions in which the method comprises: (a) providing one or more ruminant animals, (b) providing enteric fermentation-derived methane gas that has been emitted by the animals, including air containing the methane, (c) providing means to capture, consolidate, and/or direct the methane, including an enclosure means to enclose the animals, the air, and the methane contained in the air, and, preferentially, a ventilation means to direct the air, (d) providing a methane-consumption means which can use the methane as a source of carbon and/or energy for the induction of a methane-based process and/or for the production of methane-based goods, and (e) contacting the methane with the methane-consumption means to cause the methane-consumption means to oxidize, consume, and/or otherwise utilize the methane for the operation of a methane-based process or for the production of one or more methane-based products, including methane-utilizing microorganisms, heat, and/or electricity. Another embodiment of the invention pertains to the process wherein: a) one more ruminant animals are fully or partially enclosed by a well-known enclosure means, such as a barn, and b) air contained in an ruminant animal enclosure means, including the enteric fermentation methane contained therein, is further directed and exposed to a methane-consumption system, whereby enteric fermentation methane is used as a novel source of carbon and/or energy for the production of heat, electricity, or, as in one preferred embodiment, methane-utilizing microorganisms.

In one preferred embodiment, the method of the subject invention involves contacting enteric fermentation methane contained within enclosed barn air with a microbiological methane-consumption system, wherein enteric fermentation methane, methane-utilizing microorganisms, and a microorganism growth-culture medium are mutually-exposed, causing methane-utilizing microorganisms to grow using enteric fermentation methane as a source of carbon and/or energy.

FIG. 4 is a flow chart of a process carried out in accordance with the invention. In the schematic, ruminant animal 114 is situated in enclosure means 115, whereby ruminant animal 114 is substantially enclosed, isolated, and contained by and in enclosure means 115. In one preferred embodiment, enclosure means 115 includes a barn with four sidewalls and a roof.

Enclosure means 115, in one embodiment, contains enclosure air 120. Enclosure means 115 is equipped with air inlet 116 and air outlet 117, through which air, gases, and other airborne materials are substantially confined to enter and exit enclosure means 115, respectively. In one preferred embodiment, air inlet 116 consists of a spatial opening, such as a window, in a side wall of enclosure means 115, and air outlet 117 consists of a spatial opening housing ventilation means 113, through which air, gases, and other airborne material exit out of inside enclosure means 115. In one preferred embodiment, ventilation means 113 consists of a well-known ventilation fan that is used to pull air into enclosure means 115 through air inlet 116 and convey air out of enclosure means 115 through air outlet 117.

Consolidation means 118, in one embodiment, is a duct that directs enclosure air 120 coming out of air outlet 117 in such a way that it can be contacted with confined methane-utilizing microorganisms 121. In the embodiment depicted, mutual-exposure means 119 is a holding tank containing a methane-consumption means, embodied as methane-utilizing microorganisms 121, and microorganism growth-culture medium 122. In the embodiment depicted, methane-utilizing microorganisms 121 are present in growth-culture medium 122 at a concentration of 20 grams of microorganisms per liter of medium, and consist of methane-utilizing microorganisms such as *Methylococcus capsulatus* that can be obtained from any number of well known biological supply depots (including Chang Bioscience, located at 125 Cambon Drive #6H, San Francisco, Calif. 94132). Growth-culture medium 122, as herein embodied, is an aqueous medium containing suitable ammonium, mineral salts, and other well-known growth-culture components, which support the growth of methane-utilizing microorganisms 121.

The following is a description of one method by which to carry out a process in accordance with one embodiment of the invention. First, ruminant animal 114 is enclosed by enclosure means 115, and ruminant animal emits methane gas into enclosure air 120 through processes associated with enteric fermentation. Next, through the force of ventilation means 113, air is conveyed into enclosure means 115 through air inlet 116, through enclosure means 115, and out of enclosure means 115 through air outlet 117. Enclosure air 120 containing enteric fermentation methane is next conveyed out of air outlet 117, through consolidation means 118 to be contacted with methane utilizing microorganisms 121 in mutual-exposure means 119 through the force created by ventilation means 113. Inside mutual-exposure means 119, enteric fermentation methane contained within enclosure air 120 is exposed to methane-utilizing microorganisms 121 and growth-culture medium 122, causing methane-utilizing microorganisms 121 to grow and reproduce using enteric fermentation methane as a source of carbon and/or energy. The process continues when, after a certain amount of time (in this embodiment approximately 7 days) it is determined that methane-utilizing microorganisms 121 within mutual-exposure means 119 are no longer growing at optimal rates, and the microorganism growth process is augmented by removing portions of growth-culture medium 122 and methane-utilizing microorganisms 121 from mutual-exposure means 119 and adding new portions of growth-culture medium 122 and/or methane-utilizing microorganisms 121. In such a manner, enteric fermentation methane is continually used as a source of carbon and/or energy for the continuous growth and harvesting of methane-utilizing microorganisms. Finally, methane-utilizing microorganisms 121, having been grown in mutual-exposure means 119 using enteric fermentation methane as a source of carbon and/or energy, are removed from mutual-exposure means 119 and harvested as useful biomass. Such biomass can be processed and sold as a range of useful biomass-based products.

In one preferred embodiment, as described earlier, ventilation means 113 are employed to move 10 cubic feet of enclosure air 120 out of air outlet 117 each minute, such that fresh air enters into enclosure means 115 at the same rate, and enclosure air 120 is cooled by the air cooling means described earlier. As described, a dairy cow produces approximately 150 kilograms of methane per year, which correlates to the production of approximately 0.4 liters per minute of enteric fermentation methane. Thus, by enclosing ruminant animal 114 with enclosure means 115 and employing ventilation means 113, the concentration of methane in enclosure air 120 conveyed into mutual-exposure means is at least 0.1% methane by volume, or 1000 parts per million. By decreasing or increasing ventilation rates, the concentration of methane in enclosure air 120 increases or decreases accordingly. Methane-utilizing microorganisms are able to grow and reproduce using methane as a source of carbon and/or energy in an environment wherein the concentration of methane-in-air is at least 1.7 parts per million. Thus, methane-utilizing microorganisms 121 are enabled to grow and reproduce using enteric fermentation methane as a novel source of energy in one preferred embodiment.

Several embodiments of the present invention pertain to the utilization of enteric fermentation as a novel source of energy for the production of methane-based goods in a confined methane-consumption apparatus existing outside the digestive tract of a ruminant animal. There are a number of potential methods that can be used to carry out a process in accordance with embodiments of the invention. In particular, there are a number of methods that can be utilized to capture enteric fermentation methane with enclosure and ventilation means and mutually-expose enteric fermentation methane and a methane-consumption means for the purpose of causing enteric fermentation methane to be utilized as a source of carbon and/or energy.

In some embodiments, such methods include, but are not limited to, providing methane-consumption means to convert enteric fermentation methane into heat and/or electricity. In one embodiment, methane is capable of being used at a methane-in-air volumetric concentration down to abut 0.1% methane-in-air, specifically by catalytic and thermal flow-reversal reactors. Thus, systems such as these could be used as a means to utilize enteric fermentation as a viable, low-concentration source of energy in accordance with the invention. Specifically, microturbines, fuel cells, reverse-flow reactors and other means capable of utilizing methane at low concentrations can be used as a methane-consumption means in accordance with the invention, allowing enclosure air to be used in an unadulterated state as viable feedstock fuel. Gas concentrators that increase methane-in-air concentrations of exhaust gas could also be employed to increase methane concentrations to levels more suitable for use by a range of methane-consumption means. Thus, although one preferred embodiment details the use of methane-utilizing microorganism as a preferred methane-consumption means, in another embodiment, any number of methane-consumption means may be employed in accordance with embodiments of the invention to convert enteric fermentation methane into useful products such as heat and/or electricity.

In some embodiments, such methods also include the combined use of non-enteric fermentation methane and enteric fermentation methane in or by a methane-consumption means, such that enteric fermentation methane can be partially used to drive one or more methane-consumption means, such as fuel cells, turbines, microturbines, methane-utilizing microorganisms, and other methane-based systems. Such alternative sources of supplemental methane might include: methane from agricultural manure digesters, agricultural manure holding structures, landfills, coal mines, wastewater treatment facilities, and/or natural gas.

In some embodiments, such methods further include the utilization of a chemical-based methane-consumption means to use enteric fermentation methane as a source of carbon and/or energy. Specifically, a number of methods are well known to convert methane into industrial feedstock products, such as methanol, through the mutual exposure of methane and various chemicals under a variety of conditions. Suitable chemical processing methods of this nature could be applied to enteric fermentation methane in accordance with the principles of the invention, especially through the combined use of enteric fermentation methane and alternative sources of methane, as enumerated above, to increase the yields, viability, and efficiency of the process.

In several embodiments, such methods also include using methane-utilizing microorganisms to simultaneously reduce both ammonia and methane emissions from ruminant animal feedlots. In one preferred embodiment, enclosure air 120 will likely contain varying amounts of ammonia gas. It is well known that contacting ammonia gas with liquid water changes ammonia gas into aqueous ammonium, as would occur in mutual-exposure means 119 of one preferred embodiment listed above when enclosure gas 120 is contacted with growth-culture medium 122. It is well known that methane-utilizing microorganisms utilize ammonium in water as a source of nitrogen for growth. Thus, one embodiment of the invention may include the use of unadulterated enteric fermentation to not only produce methane-utilizing microorganisms, but to simultaneously reduce feedlot ammonia emissions as well.

In some embodiments, such methods also include using enclosure means and/or methane-consumption means, as detailed above, to reduce dust or suspended particles emissions associated with ruminant animals. In order to increase the efficiency of a methane-driven system as detailed above, a filter may be used to prevent dust and/or other airborne particles from entering into mutual exposure means 119. Thus, a process employed in accordance with the invention may be used to reduce enteric fermentation methane emissions while simultaneously reducing emissions of suspended particles typically associated with ruminant animals.

In some embodiments, such methods further include providing means to convey enclosure air 120 from areas enclosed by enclosure means 115 where enteric fermentation methane is known to accumulate, such as near feeding tracts, roof lines, or other potential methane accumulation areas. Such methods also include situating a means for mutual-exposure containing a methane-consumption means inside of an area enclosed an enclosure means, wherein means may or may not be provided to continuously or mechanically direct enclosure air to contact a methane-consumption system, but in either case causing enteric fermentation to be utilized as a source of energy for the production of methane-based goods.

In one embodiment, enteric fermentation methane is used as a novel source of energy for the production of methane-utilizing microorganisms in a confined growth-and-harvest apparatus existing outside of the digestive tract of a ruminant animal. There are a number of potential methods that can be used to carry out a process in accordance with the invention. In particular, there are a number of methods that can be used to mutually-expose enteric fermentation methane, methane-utilizing microorganisms, and a microorganism growth-culture medium for the purpose of causing methane-utilizing microorganisms to grow using enteric fermentation methane as a source of carbon and/or energy.

In some embodiments, such methods include confining a ruminant animal to a site provided with means to funnel, convey, and/or direct enteric fermentation methane into an apparatus whereby such enteric fermentation methane is used to grow methane-utilizing microorganisms in a confined apparatus, and whereby the means used to carry out this process are either partially situated on a ruminant animal or not at all situated on a ruminant animal.

In some embodiments, such methods also include providing means to convey enteric fermentation methane from a site where ruminant animals are known to frequent, such as feeding or sleeping areas, to a means for the mutual-exposure of enteric fermentation methane, methane-utilizing microorganisms, and a microorganism growth-culture medium, whereby methane-utilizing microorganisms grow using enteric fermentation methane as a source of carbon and/or energy in an apparatus existing outside of the digestive tract of a ruminant animal.

In some embodiments, such methods also include causing methane-utilizing microorganisms to grow by mutually-exposing enteric fermentation methane, methane-utilizing microorganisms, and a microorganism growth-culture medium in a confined apparatus, wherein some or all of the methane-utilizing microorganisms are genetically-engineered.

In some embodiments, such methods also include growing methane-utilizing microorganisms using enteric fermentation methane as a source of carbon and/or energy for such growth, whereby the means used to carry out the process are powered by solar, wind, methane-based, or other suitable form of power different from the source of power—battery power—mentioned in the above detailed description.

There are also a number of methods in accordance with several embodiments of the invention that can be used to mutually-expose enteric fermentation methane, methane-utilizing microorganisms, and a microorganism growth-culture medium for the purpose of causing methane-consumption systems to operate using enteric fermentation methane as a source of carbon and/or energy.

In some embodiments, such methods also include collecting, storing, and/or transporting ruminant animal methane (or gaseous emissions from non-animal sources) for later use in a process carried out in accordance with the invention.

The following Example illustrates some embodiments of the present invention and is not intended in any way to limit the invention. Moreover, the methods described in the following example need not be performed in the sequence presented.

EXAMPLE 1

The following example describes the processing of methane emissions from a landfill site. One of skill in the art will understand that the method described herein can also be used for any site that produces methane, such as coal mines, wastewater treatment plants, manure digesters, agricultural digesters, compost heaps, or enclosed agricultural feedlots.

In one embodiment, a landfill site that produces methane emissions will be identified. Landfill gas extraction wells and blowers are employed to draw landfill gas out of the landfill using equipment and technology that is used by any landfill gas extraction or environmental services firm, such as LFG Technologies of Fairport, N.Y., USA or SCS Engineers of Long Beach, Calif., USA. The methane content of the extracted landfill gas can be monitored for the production of methane using any methane detector commonly used by an environmental services firm. If the methane concentration is greater than about 1%, the landfill will be deemed suitable for methane recovery and processing. In some embodiments, the methane concentration is between about 10% and 60%, more preferably between 40% and 50%. In other embodiments, methane emissions comprise methane in a concentration in the range of about 0.1% to about 10%, in the range of about 10% to about 20%, or in the range of about 20% to about 40%, or greater than about 20%. Landfill sites (or other sites) having methane concentrations less than 1% and greater than 60% may also be used in some embodiments of the invention.

After a suitable landfill site has been identified, the landfill gas will be captured from the landfill using an air compressor, blower, vacuum, or other suitable capturing means. Impurities will then be removed from the landfill gas. For example, non-methane organic compounds can be removed by passing the landfill gas through activated carbon, leaving mostly methane and carbon dioxide as the main components of the landfill gas. Although impurities need not be removed in every embodiment of the invention, the removal of impurities is advantageous in some embodiments. One advantage of removing impurities (such as water vapor, volatile organic compounds, particulate materials, and/or carbon dioxide) is minimizing the possibility of hindering microorganism growth as microorganisms contact the landfill gas.

The landfill gas is optionally disinfected using UV light. In those embodiments in which impurities are removed, UV irradiation can be used before, after or during the removal process. UV irradiation may also be used in embodiments that do not employ impurities removal. UV light is believed to disinfect the landfill gas by disrupting the nucleic acid structures within microorganisms in the landfill gas, subsequently eliminating the capacity of these microorganisms to reproduce. Impurities removal and disinfection do not have to be employed, however, because methanotrophic microorganisms can withstand a range of impurities.

The landfill gas (which in a preferred embodiment is purified and disinfected) as well as air or oxygen (which in one embodiment is purified and/or disinfected) will be fed into a self-contained enclosure using an air compressor, air blower, or similar means. The self-contained enclosure is preferably a bioreactor that contains at least one species of methanotrophic microorganisms and growth medium. The bioreactor is preferably sized to accommodate the flow rate of landfill gas to be treated. For example, a bioreactor treating 1000 cubic feet per minute of landfill gas should be approximately twice as large in volume as a bioreactor treating 500 cubic feet per minute of landfill gas. Preferably, a bioreactor treating 1000 cubic per minute of landfill gas will contain about 100,000-800,000 liters of growth medium containing suspended methanotrophic microorganisms. Growth medium can be a liquid, semi-liquid, or solid substrate. For example, the growth medium may be water containing growth nutrients such as nitrogen and trace minerals, in which microorganisms are suspended.

In one embodiment, the growth medium can be tailored to meet the specification of the end-product of microorganism growth. If the bioreactor is being used to create soluble methane monooxygenase, for example, it will be preferable to keep the copper concentration in the growth medium sufficiently low, for example, below about $5 \times 10^{-9}$ M, which may be achieved through continuous monitoring of the growth medium and calculated metering of copper into the growth medium.

The growth medium solution may consist of water filled with a range of mineral salts. For example, each liter of growth medium may be comprised of 1 g $KH_2PO_4$, 1 g $K_2HPO_4$, 1 g $KNO_3$, 1 g NaCl, 0.2 g $MgSO_4$, 26 mg $CaCl_2*2H_2O$, 5.2 mg EDTA $Na_4(H_2O)_2$, 1.5 mg $FeCl_2*4H_2O$, 0.12 mg $CoCl_2*6H_2O$, 0.1 mg $MnCl_2*2H_2O$, 0.07 mg $ZnCl_2$, 0.06 mg $H_3BO_3$, 0.025 mg $NiCl_2*6H_2O$, 0.025 mg $NaMoO_4*2H_2O$, 0.015 mg $CuCl_2*2H_2O$, or a combination thereof. In another embodiment, the growth medium comprises solid and/or liquid media. In yet another embodiment, the growth medium comprises agar.

Methanotrophic microorganisms may be present in the bioreactor in any concentration. Preferably, in one embodiment, there are about 1 to 100 grams of microorganisms per liter of water (or other aqueous solution) in the bioreactor, preferably about 10-50 grams per liter, more preferably about 40-50 grams per liter, over the course of treatment. The methanotrophic microorganisms are exposed to the methane within landfill gas for about 1-200 hours, preferably about 24-96 hours, whereupon a portion of the microorganisms within the bioreactor, preferably about 10-50%, are removed and replaced with fresh growth media or growth media containing a low concentration of microorganisms, in order to allow more methanotrophic microorganisms to grow in the bioreactor and continue to treat the methane within the landfill gas at high rates.

The microorganisms that are removed from the bioreactor are processed further according to the specification of the end-product of microorganism growth. For example, if the microorganism biomass is to be used directly as a protein source, the suspended biomass may be dewatered in a belt filter press, bag filter, spray drier, and/or centrifuge, all of which may be used to reduce the water content of the biomass, preferably below about 10-20% total biomass weight. If the microorganism biomass is to be used to generate a polymer such as PHB, the microorganisms may be exposed to a bioreactor receiving a continuous supply of landfill gas and air or oxygen, wherein the growth medium is deprived of a specific essential nutrient, such as nitrogen, in order to cause the microorganisms to synthesize intracellular PHB. After a period of about 1-3 days, some portion of the bioreactor may then be removed in order to harvest the products of bioreactor growth, in this case PHB. PHB may be harvested through a variety of well known cell extraction and polymer purification techniques. Dewatering methods may include, but are not limited to, the use of centrifuges, spray driers, or belt filter presses. Cell lysis and cell parts separation methods may include, but are not limited to, the use of hot chloroform, sodium hydroxide, cell freezing, sonication, and homogenization. For homogenization, the pressure drop is preferably between about 5000 and 10,000 bar to effect sufficient cellular lysis. For the use of sodium hydroxide, the concentration of sodium hydroxide is preferably raised to approximately 2 M. Isolated, dried, and harvested microorganism product, such as biomass, polymer, or enzyme, may be used or sold for use.

While the above description of preferred systems and methods of carrying out processes in accordance with embodiments of invention contains many specificities, these should not be construed as limitations on the scope of the invention. As stated, there are a number of ways to carry out a process in accordance with invention. Accordingly, the scope of the invention should be determined not by the preferred systems and methods described, but by the appended claims and their legal equivalents.

What is claimed is:

1. A method of producing a polyhydroxyalkanoate (PHA) and a methane monooxygenase (MMO) in a culture of methanotrophic microorganisms in the presence of non-methane organic compounds, the method comprising:
    a) providing a gaseous emission, wherein said gaseous emission comprises methane and one or more non-methane organic compounds;
    b) providing a microorganism culture medium, wherein said culture medium comprises copper, one or more of nitrogen, magnesium, phosphorus, oxygen, carbon, potassium, and/or iron, and a culture of methanotrophic microorganisms that can metabolize said methane and said one or more non-methane organic compounds;
    c) exposing said gaseous emission to said culture;
    d) adjusting the concentration of copper in said culture medium to a concentration sufficient to effect production of particulate methane monooxygenase (pMMO) or soluble methane monooxygenase (sMMO) by said culture of methanotrophic microorganisms; and
    e) depleting said culture medium of nitrogen, wherein said depletion causes said culture of methanotrophic microorganisms within said culture medium to generate said polyhydroxyalkanoate (PHA).

2. The method of claim 1, wherein said PHA is selected from the group consisting of one or more of the following: polyhydroxybutyrate (PHB) and polyhydroxybutyrate-valerate (PHB/V).

3. The method of claim 1, further comprising removing impurities from said gaseous emission.

4. The method of claim 1, wherein said gaseous emission comprises methane at a concentration in the range of about 0.1% to about 60%.

5. The method of claim 1, wherein said gaseous emission is generated by a source selected from the group consisting of one or more of the following: coal mine, wastewater treatment operation, agricultural digester, enclosed feedlot, petroleum transport system, petroleum recovery system, landfill, ruminant animal, and compost facility.

6. The method of claim 1, wherein said culture of methanotrophic microorganisms comprises at least one of a naturally-occurring or genetically-modified microorganism that uses methane as a source of carbon or energy for growth or reproduction.

7. The method of claim 1, wherein said one or more non-methane organic compounds are partially or fully metabolized by said culture of methanotrophic microorganisms.

8. The method of claim 1, wherein said one or more non-methane organic compounds are partially or fully oxidized by said culture of methanotrophic microorganisms.

9. A system for producing a polyhydroxyalkanoate (PHA) and a methane monooxygenase (MMO) in a culture of methanotrophic microorganisms in the presence of non-methane organic compounds, comprising:
   a) a source of gaseous emissions, wherein said gaseous emissions comprise methane, and at least one non-methane organic compound that influences the metabolism of methanotrophic microorganisms;
   b) a culture of methanotrophic microorganisms, wherein said microorganisms are capable of metabolizing said methane and said non-methane organic compound;
   c) a culture medium, comprising copper and one or more of nitrogen, magnesium, phosphorus, oxygen, carbon, potassium, and/or iron;
   d) a bioreactor that encloses or contains said gaseous emissions and said culture medium; and
   e) a conveyer that conveys said gaseous emissions into said bioreactor, wherein the concentration of copper in said culture medium is adjusted to a concentration sufficient to effect production of particulate methane monooxygenase (pMMO) or soluble methane monooxygenase (sMMO) by said methanotrophic microorganisms, and wherein the nitrogen in said culture medium is depleted, and wherein said depletion causes said culture of methanotrophic microorganisms to use a portion of said methane in the presence of said non-methane organic compounds to generate a polyhydroxyalkanoate (PHA).

10. The system of claim 9, wherein said gaseous emissions comprises methane at a concentration in the range of about 0.1% to about 60%.

11. The system of claim 9, wherein said gaseous emissions are generated by a source selected from the group consisting of one or more of the following: coal mine, wastewater treatment operation, agricultural digester, enclosed feedlot, petroleum transport system, petroleum recovery system, landfill, ruminant animal, and compost facility.

12. The system of claim 9, wherein said culture of methanotrophic microorganisms comprises at least one of a naturally-occurring or genetically-modified microorganism that uses methane as a source of carbon or energy for growth or reproduction.

13. The system of claim 9, wherein said culture of methanotrophic microorganisms comprises at least two different species of methanotrophic microorganisms.

* * * * *